United States Patent
Wagner

(10) Patent No.: US 11,241,326 B2
(45) Date of Patent: Feb. 8, 2022

(54) DYNAMIC CORRECTION SPLINT

(71) Applicant: Helmut Wagner, Duderstadt (DE)

(72) Inventor: Helmut Wagner, Duderstadt (DE)

( * ) Notice: Subject to any disclaimer, the term of this patent is extended or adjusted under 35 U.S.C. 154(b) by 641 days.

(21) Appl. No.: 15/670,662

(22) Filed: Aug. 7, 2017

(65) Prior Publication Data
US 2018/0042748 A1    Feb. 15, 2018

(30) Foreign Application Priority Data
Aug. 10, 2016 (DE) .................. 20 2016 104 405.7

(51) Int. Cl.
*A61F 5/01* (2006.01)
*A61F 5/058* (2006.01)

(52) U.S. Cl.
CPC .......... *A61F 5/0102* (2013.01); *A61F 5/0125* (2013.01); *A61F 5/058* (2013.01); *A61F 5/013* (2013.01); *A61F 2005/0132* (2013.01); *A61F 2005/0167* (2013.01); *A61F 2005/0179* (2013.01)

(58) Field of Classification Search
CPC ...... A61F 5/0102; A61F 5/0125; A61F 5/058; A61F 5/013; A61F 2005/0132; A61F 2005/0167; A61F 2005/0179
See application file for complete search history.

(56) References Cited

U.S. PATENT DOCUMENTS 4,846,842 A * 7/1989 Connolly ............... A61F 5/0125
   623/43
5,409,449 A * 4/1995 Nebolon ............... A61F 5/0125
   16/333

(Continued)

FOREIGN PATENT DOCUMENTS

DE    84 33 416 U1    2/1985
DE    35 35 578 A1    5/1986

(Continued)

OTHER PUBLICATIONS

Website: www.caroli.de/en/dynamic-joint-braces, downloaded Aug. 7, 2017 (4 Pages).

(Continued)

*Primary Examiner* — Camtu T Nguyen
(74) *Attorney, Agent, or Firm* — Smith Tempel Blaha LLC; Daniel J. Santos

(57) ABSTRACT

The invention relates to a dynamic correction splint (1) with two splint parts (5, 6) connected to each other via a joint (2). Spring bases (25, 26) of a spring device (27) are each coupled to a splint part (5, 6) in such a way that pivoting the splint parts (5, 6) leads to an altered biasing of the spring device (27). The spring device (27) exerts a correction moment onto the splint parts (5, 6) acting in the direction of a correction position of the splint parts (5, 6). The spring device (27) is configured and coupled to the splint parts (5, 6) in such a way that the absolute value of the correction moment increases as the correction position of the splint parts (5, 6) is approached. It is possible that a switching mechanism (40) is present. The switching mechanism (40) is actuated in a motion-controlled way by the pivoting of the splint parts (5, 6) and at its actuation changes the coupling of the splint parts (5, 6) with the spring device (27).

11 Claims, 28 Drawing Sheets

(56) References Cited

U.S. PATENT DOCUMENTS

| | | | |
|---|---|---|---|
| 5,443,444 A * | 8/1995 | Pruyssers | A61F 5/0123 602/16 |
| 5,472,410 A * | 12/1995 | Hamersly | A61F 5/0125 601/33 |
| 5,575,764 A | 11/1996 | Van Dyne | |
| 5,814,000 A * | 9/1998 | Kilbey | A61F 5/0125 602/16 |
| 7,534,216 B2 | 5/2009 | Jacobs | |
| 8,882,688 B1 * | 11/2014 | Ancinec | A61F 5/0125 128/882 |
| 2002/0094919 A1 | 7/2002 | Rennex et al. | |
| 2009/0198161 A1 | 8/2009 | Seligman | |
| 2012/0071803 A1 | 3/2012 | Jansson | |
| 2014/0276304 A1 | 9/2014 | Dollar et al. | |

FOREIGN PATENT DOCUMENTS

| | | |
|---|---|---|
| DE | 87 04 851 U1 | 7/1987 |
| DE | 199 04 554 B4 | 8/2000 |
| DE | 201 17 080 U1 | 1/2002 |
| EP | 2 959 869 A1 | 6/2015 |
| WO | WO2005/076882 * | 8/2005 |
| WO | 2016/210121 A1 | 12/2016 |

OTHER PUBLICATIONS

Website: www.prowalk.de/neurologie-orthopaedie/ultraflex, cp. the product with the labels "Ultraflex" and "ONE", downloaded Aug. 7, 2017 (2 Pages).

Website: http://basko.com/index.aspx?lang=en; cp. product "MultiMotion", downloaded Aug. 7, 2017 (3 pages).

http://www.ottobock.de/media/lokale-medien-de_de/prothetik/neuro-orthop%C3%A4die.pdf (pp. 180-183).

European Search Report in co-pending, related EP Application No. 17184729.6, dated Dec. 18, 2017.

* cited by examiner

DYNAMIC CORRECTION SPLINT

CROSS REFERENCE TO RELATED APPLICATIONS

This application claims priority to co-pending German Utility Model Application No. DE 20 2016 104 405.7 filed Aug. 10, 2016.

FIELD OF THE INVENTION

The invention relates to a dynamic correction splint. A dynamic correction splint is a dynamic joint splint which could also be called a dynamic redression orthosis. Dynamic correction splints of the present type are in one embodiment in particular also known as a so-called "Quengel splint". Dynamic correction splints can be used to treat a joint with limited mobility between parts of an extremity of the human or animal body. By means of the dynamic correction splint, a correction movement can be exerted on the parts of the extremity in the direction of the limitation of mobility or a tension can be exerted opposing the direction of a contracture. It is also possible that the dynamic correction splint is used for post-treatment of a tendon injury. In this case the correction moment of the dynamic correction splint serves for relieving the operatively treated tendon. The dynamic correction splint can also be used for any extremity and corresponding joints, a wrist joint, a finger joint, an elbow joint, a knee joint, an ankle joint, a hip joint or similar. Possible medical indications for the use of a dynamic correction splint may be (without limitation to these) an orthotic treatment with limited mobility, a treatment after injuries with contractures, a treatment after surgery, a mobilization of a joint step-by-step, a treatment of spastic musculature threatened by shortening, use for an extension or a flexion, a treatment of patients with spasticities to stimulate motion and counter malpositions and contractures caused by spasticity, neurological indications such as cerebral paresis, a stroke, a spinal canal injury, multiple sclerosis, spina bifida, cranial cerebral injury, muscular dystrophy, arthrogryposis, orthopaedic indications after a total knee prosthesis, amputations, operations, injuries of ligaments or fractures. Within the framework of the invention, the dynamic correction splint can also form an attachment which supplements a conventional pivoting splint. While in a conventional pivoting splint splint parts are usually only connected to each other by a joint, but no correction moment is created, the dynamic correction splint forming the attachment possesses splint parts which can be joined by suitable fixing means (screws, in the simplest case) to splint parts of the pivoting splint. By means of the dynamic correction splint forming the attachment, the necessary correction moment is created which is then transferred by the fixing means to the pivoting splint.

Dynamic correction splints of the kind present here comprise two splint parts connected to each other pivotably by a joint. The splint parts can each be attached to a part of an extremity in such a way that the splint parts are also pivoted when the parts of the extremity are pivoted. While for the indications given above in a starting position of the dynamic correction splint generally no correction moment is necessary, it is desired for the dynamic correction splint to create a correction moment acting in the direction of the correction position when a correction position is approached.

In the following, for a simplified explanation and as an example a dynamic correction splint or Quengel splint for an elbow will be referred to which is used after an operative treatment of a tendon involved in stretching the elbow (without the invention being intended to be limited with respect to the field of use for an elbow or with respect to a treatment of a tendon after a surgery):

For the example mentioned, a starting position of the elbow joint is a maximum bent position of the forearm with respect to the upper arm for which the forearm and the upper arm form a bending angle of approx. 140° with respect to the straightened position. The correction position of the dynamic correction splint, on the contrary, in this case corresponds to the maximum straightened position, that is, a bending angle of 0° of the forearm with respect to the upper arm. It is also possible that during the successive treatments under use of the dynamic correction splint the straightened position is successively reduced from a first straightened angle of e.g. 25° in a plurality of steps to the last straightened angle of 0°. If after the surgery the moment applied via the straightening tendon is not enough to bring the elbow joint into the straightened position or if the straightening only by means of the straightening tendon endangers the operative result, it is desired for the dynamic correction splint to create a correction moment which acts in the direction of the correction position when the straightened position, that is, the correction position, is approached and which therefore induces a straightening of the elbow joint or supports the straightening by the straightening tendon.

In known dynamic correction splints, between the splint parts a torsion spring is used which is pre-tensioned in such a way that in the correction position it creates the necessary correction moment. This torsion spring has to be tensioned further with the motion out of the correction position in the direction of the starting position so that for the pivoting of the forearm in the direction of the bent position, that is, for a flexion, the muscles involved in the bending have to create an increased bending moment which, depending on the characteristic of the torsion spring, increases linearly or in a curve at an increase of the bending angle.

BACKGROUND OF THE INVENTION

Dynamic correction splints are for example known from
the web page www.caroli.de/dynamische-gelenkschienen (English: www.caroli.de/en/dynamic-joint-braces; date of inspection: Jul. 28, 2016),
the web page www.prowalk.de/neurologie-orthopaedie/ultraflex (date of inspection: Jul. 28, 2016), cp. the product with the labels "Ultraflex" and "ONE" (registered trademarks),
the web page www.basko.com (English: http://basko.com/index.aspx?lang=en; cp. product "MultiMotion", date of inspection: Jul. 28, 2016),
the product leaflet of Otto Bock HealthCare GmbH company titled "Neuro-Orthopädie", http://www.ottobock.de/media/lokale-medien-de_de/prothetik/neuro-orthop%C3%A4die.pdf, chapter on other components, arm splints to correction joint systems, (pages 180-183), and The documents DE 87 04 851 U1 and DE 84 33 416 U1 disclose static dynamic correction splints for fixing a pivoting angle of the extremities.

DE 199 04 554 B4 discloses the use of a dynamic correction splint and a follower splint which are arranged on opposite sides of an elbow and which are each fixed to the forearm and the upper arm with their corresponding side parts by a fixing strap. The dynamic correction splint in this context is intended to allow a correction effect in the flexion direction and the extension direction. Via a worm shaft, a limitation of the maximum flexion and extension can be set. Eccentrically from the pivoting axis of the dynamic correction splint, an end region of a coupling rod is linked to a supporting disc. The other end region of the coupling rod is supported on the distal splint part in an axially slidable way against a spring. In the neighborhood of the straightened position, the spring-biased coupling rod causes a correction moment directed towards the straightened position. With an increasing approach to the straightened position the correction moment decreases. If (with increasing muscular strength of the wearer of the dynamic correction splint) starting from the straightened position a bending of the dynamic correction splint occurs, the effective axis of the coupling rod changes until for a medium pivoting angle the effective axis of the coupling rod runs through the pivoting axis of the dynamic correction splint. At a further increase of the bending angle, the direction of the correction moment reverses. Even at an increase of the bending angle and an approach to the maximum bending position, the absolute value of the correction moment increases.

DE 201 17 080 U1 (corresponding to U.S. Pat. No. 7,534,216 B2) discloses a dynamic correction splint in which the correction moment comprises a pneumatic actuating cylinder. The pressure biasing the pneumatic actuating cylinder can be influenced by means of an electronic control device, in which way an electronic control of the correction moment is possible.

SUMMARY OF THE INVENTION

It is an object of the invention to propose a dynamic correction splint which comprises an alternative or improved characteristic of the correction moment in dependence on the pivoting angle of the dynamic correction splint, which is to be guaranteed especially with simple construction.

For one embodiment of the invention, the dynamic correction splint comprises two splint parts and one spring device (generally with any possible construction). The spring bases of the spring device are each coupled to one of the splint parts. The coupling is done in such a way that a pivoting of the splint parts leads to an altered biasing of the spring device. Preferably, (at least in a pivoting subrange) the spring device is linked to the two side parts (directly or indirectly) so that the motion of a spring base corresponds to the motion of the splint part. The spring device exerts a correction moment onto the splint parts acting towards a correction position of the splint parts. The correction position is especially a position with maximum extension or a straightened position or a maximum flexion.

For one embodiment of the invention, it is suggested to realize the spring device in such a way and to couple it to the splint parts in such a way that the absolute value of the correction moment increases with an approach to the correction position of the spring parts. In other words, according to this embodiment of the invention the correction moment is larger in the correction position than in a pivoting position of the splint parts (directly) neighboring the correction position. Preferably, the correction moment is larger in the correction position than for all possible other pivoting angles of the splint parts. In the correction position, the characteristic of the absolute value of the correction moment has an absolute or relative maximum.

Due to one embodiment of the invention, a characteristic of the correction moment is used which has as a result that for a motion of the dynamic correction splint away from the correction position the user has to apply decreasing muscular strengths, in which way the wearing comfort is improved.

Possibly, the therapeutic effect of the dynamic correction splint can also be improved if the correction moment increases when coming closer to the correction position.

In the dynamic correction splint according to one embodiment of the invention, a pair of splint parts, the connecting joint and the spring device directly form the orthotic or splint, which extend in parallel to the parts of the extremity of the person. At their ends the splint parts are connected to the parts of the extremity. However, it is also possible that the splint parts are those parts of the dynamic correction splint to which the additional splints extending parallel to the extremities of the person wearing the dynamic correction splint are fixed. In this case or in the case of a realization of the dynamic correction splint as an attachment for a pivoting splint, the dynamic correction splint according to this embodiment of the invention forms a partial construction unit which can be mounted with other parts (such as the aforementioned splints) or with other partial construction units, such as the pivoting splint, to form an orthosis.

According to one embodiment of the invention, it is furthermore suggested for the dynamic correction splint to comprise a switching mechanism. In a motion-controlled way the switching mechanism is actuated by the pivoting of the spring parts. Due to the actuation of the switching mechanism, the coupling of the splint parts with the spring device is altered, in which way the characteristic of the correction moment is influenced. For the kind of alteration of the coupling of the splint parts with the spring device caused by the switching mechanism there are multitudinous possibilities. Without a limitation of the invention to the following examples, it is mentioned in an exemplary way that it is possible that with a non-actuated switching mechanism at least one splint part may not be coupled to the spring device while at the actuation of the switching mechanism the two splint parts can each be (directly or indirectly) coupled to a spring base of the spring device. To mention only another, non-limiting example for the switching mechanism, the alteration of the coupling of the spring parts with the spring device can be that for a switching state of the switching mechanism first spring bases of the spring device can be used while for another switching state of the switching mechanism other spring bases of the spring device can be used so that, for example, different parts of the spring device or different effective spring lengths of the spring device are used. It is also possible that for one switching state of the switching mechanism only a coupling of the splint parts to the spring bases of the spring device occurs while the portion of the spring device arranged between the spring bases is free without additional forces being exerted by the splint parts here. In this case, in the other switching state of the switching mechanism an additional coupling or an effective connection between the spring device at a place between the two spring bases and one of the splint parts can be brought about, for example by fixing the spring device at this place and/or a deflection of the spring device at this place. It is also possible, for example, that in a switching state of the switching device the spring device creates a correction moment acting in the direction of the correction position and effective onto the splint parts, the absolute value of which depends on the pivoting angle of the splint parts and which increases as the correction position is approached. Instead, in the other switching state of the switching device the spring device creates a correction moment also acting in the direction of the correction position and effective onto the splint parts, the absolute value of which is constant independently of the pivoting angle of the splint parts, or even does not create a correction moment at all.

The correction position preferably is a maximum bending position, that is, a position with a maximum bending angle of the two splint parts or a straightened position or a position of the splint parts with maximum extension (an overextension may also be possible). Therefore, the correction moment can act either in the direction of a flexion or in the direction of an extension. For one proposal of the invention, the correction position is the straightened position of the splint parts while alternatively or cumulatively a starting position of the dynamic correction splint is a maximum bending position of the splint parts with a maximum bending angle of the splint parts.

In a further embodiment of the invention, the dynamic correction splint comprises at least one stop by which the correction position and/or the starting position is set. A fixed pivoting angle can be assigned to the stop. It is also possible that the stop is adjustable, in which way an adjustment of the correction position and/or the starting position is possible.

Preferably, in the correction position and/or in the starting position the spring device biases a splint part against the stop. Here, the stop can for example be formed by the other splint part or supported by the other splint part.

An influencing of the characteristic of the correction moment can be achieved in various ways. For example, via the choice of the spring stiffness and/or a non-linearity of the spring stiffness in dependence on the pivoting angle an influencing of the characteristics of the correction moment can be achieved. It is also possible that spring bases of the spring device are arranged on the splint parts of the dynamic correction splint in such a way that the alteration of the distance of the spring bases is dependent in a non-linear way on the pivoting angle of the splint parts. It is also possible that the spring bases are not held fixed on the splint parts but are held on a supporting body. In this case it is possible that the relative position or angle of the supporting body relative to the splint part changes when pivoting of the splint parts.

For another embodiment of the dynamic correction splint according to the invention, it is suggested for the dynamic correction splint to comprise a first pivoting range and a second pivoting range. The first pivoting range neighbors the correction position or it includes the correction position at its edge. In this first pivoting range, the splint parts are coupled to the spring device via a first coupling. The second pivoting range neighbors the starting position or includes the starting position at its edge. In the second pivoting range, the splint parts are coupled to the spring device via a second coupling. The second coupling and the first coupling differ from each other. A transition (which can be achieved at a discrete pivoting angle or when reaching a second pivoting angle range) from the first pivoting range to the second pivoting range (and/or the other way around) is achieved via an actuation of the switching mechanism. The switching mechanism in a motion-controlled way is actuated by the pivoting of the splint parts.

Generally, the characteristic of the correction moment can be of any kind. In a special embodiment of the invention, it is suggested for the correction moment in the second pivoting range to be constant, zero and/or at maximum 30% (preferably at maximum 20% or at maximum 10%) of the mean of the absolute value of the correction moment in the first pivoting range. This embodiment especially bases on the finding that (among other things) the effect of the correction moment is only desired in the first pivoting range, that is, in the environment of the correction position, while a possible correction moment in the second pivoting range has to be accepted as a "necessary evil", since the user has to apply or surpass a moment for a pivoting in the second pivoting range. If in this second pivoting range the correction moment is constant, zero or comparatively small, this possibly increases the wearing comfort of the dynamic correction splint.

Generally, the characteristic of the correction moment, the spring device and/or the coupling of the spring device to the splint parts (apart from a possible switching mechanism) can be set fixedly by the manufacturer. For example, to enable an adaptability to a usage of the dynamic correction splint for different places of employment on the human body, for different kinematic conditions and dimensions of the extremities and the corresponding joint and/or different injuries or for different kinds of surgery and healing steps, according to a further proposal of the invention, however, the characteristics of the correction moment, the spring device and/or the coupling of the spring device to the splint parts are adjustable. An adjustment is possible in steps or as a continuous adjustment.

For a constructive realization of the dynamic correction splint, spring bases of the spring device are each coupled with an eccentricity with respect to a pivoting axis of the spring parts to a corresponding spring part. In the partial range in which the absolute value of the correction moment increases with increasing approach to the correction position, for this embodiment the splint parts are arranged with an angle which is larger than 180°. At the same time, the angle of connecting axes of the spring bases of the spring device with the pivoting axis of the dynamic correction splint are smaller than 180°. It is possible that a spring base fixed to a splint part on one side is arranged with a distance to a longitudinal axis of the other splint part, while the base body of the first-mentioned splint part then extends on the other side of the mentioned longitudinal axis. It is possible that the angle of the connecting axis of the spring bases with respect to the pivoting axis decreases with increasing distance from the correction position. This results in the lever arm of the spring device increasing, in which way then the increasing correction moment can be created.

For a further proposal, in the dynamic correction splint as the spring device a longitudinal spring is employed. This is a spring loaded with a normal force or longitudinal force, for example a tension spring, a pressure spring, an elastic band or similar. In such a longitudinal spring, the spring force depends on an elongation of the longitudinal spring in the longitudinal direction. For this embodiment of the spring device, the switching mechanism can be that in the first pivoting range the longitudinal spring is only coupled to the splint parts via the spring bases of the longitudinal spring. Preferably, in the first pivoting range the spring bases are directly linked to a splint part or a supporting body mounted to it. On the contrary, in the second pivoting range the longitudinal spring is additionally supported at a location between the two spring bases on a support. The support is preferably held or realized by one of the splint parts. In the region of the support, a deflection of the longitudinal spring occurs. By the deflection the coupling of the spring device to the splint parts changes and the spring characteristic alters in dependence on the pivoting angle of the splint parts. For this embodiment, the actuation of the switching mechanism therefore is provided by the creation of the contact of the longitudinal spring with the support, which is achieved in a motion-controlled way with the motion of the splint parts.

Depending on the location of the support, in any chosen way an influence can be taken on the characteristic of the correction moment. For a special proposal of the invention, the additional support of the longitudinal spring is arranged in the region of the pivoting axis of the splint parts. This leads to the result that the effective axes of the two partial portions of the longitudinal spring separated by the support (so on the one hand the partial portion between a first spring base and the support and on the other hand the partial region between a second spring base and the support) each run through the pivoting axis (or with only a small distance from it), so that the spring force of the longitudinal spring in these two partial ranges has no (or a small) lever arm. The results in a correction moment of zero or a correction moment that is small corresponding to the size of the lever arm being created in the second pivoting range, which for the user facilitates a pivoting in the second pivoting range.

For such an embodiment, the linking of the spring base of the longitudinal spring to the splint parts does not change over the complete pivoting of the splint parts, so that the linking is independent of the actuation of the switching mechanism. For an alternative or cumulative proposal, the switching mechanism couples a spring base of the spring device (or a supporting body supporting the same) to one of the splint parts in the first pivoting range. This results in a motion of the spring base occurring with the pivoting of the splint parts, which goes along with a change of the biasing of the spring device, which is in turn coupled to the correction moment increasing in the direction of the correction position. On the contrary, the switching mechanism uncouples the spring base of the spring device (or a supporting body supporting the same) from the splint part in the second switching state of the switching mechanism corresponding to the second pivoting range. This results in a relative motion of the splint parts without there being a motion of the spring base or the supporting body so that there is no change of the correction moment.

For the design of the switching mechanism for providing this functionality there are multitudinous possibilities: For example, there can be an elongated hole present in which a coupling body can move freely in the second pivoting range, while in the first pivoting range the coupling body rests against an edge-sided boundary of the elongated hole. It is also possible that the switching mechanism is realized as a latching or locking device effective between the spring base or the supporting body and the corresponding splint part. Here, in a motion-controlled way the switching mechanism can be unlatched or unlocked by the pivoting of the splint parts. For a special proposal of the invention, in the first pivoting range the splint part is coupled by a coupling body in a form-locking way to the spring base or to the supporting body. In the second pivoting range, the form-locking coupling between the splint part and the spring base or the supporting body has been removed.

It is possible that for a form-lock in the first pivoting range the coupling body is arranged in recesses of the splint part and/or the spring base or the supporting body. On the contrary, for the transition from the first pivoting range to the second pivoting range the coupling body is moved in a motion-controlled way by the pivoting of the splint parts out of the recess of the splints part and/or the spring base or the supporting body.

Generally, the dynamic correction splint can be manufactured with any construction element in any manufacturing process. It is possible, for example, that the splint parts and/or the supporting body are forged parts or cast parts. Any material can be used in this respect, especially a high-strength or fiber-reinforced plastic, aluminum, titanium or steel. Preferably, the splint parts and/or the supporting body are realized by a panel construction (especially with metallic panels or sheets), where the splint parts and the supporting body can directly rest against each other in the region of the joint of the dynamic correction splint. It is also possible that between parts moved or pivoted with respect to one additional sliding bodies or sliding discs, sliding coatings or other sliding bodies are arranged.

The object of the claims are dynamic correction splints of the kind explained before. The claims also comprise the realization of the dynamic correction splint as a kind of attachment which can be attached to splints bars of a pivoting splint of any kind via splint parts as splint bars (which can be formed in any way and do not have to be realized as elongated bars or struts). The orthosis comprised of the attachment formed by the dynamic correction splint and the pivoting splint then creates the necessary correction moment. It is possible that a connection of the splint parts of the dynamic correction splint and the splint parts of the pivoting splint is achieved in a fixed, given orientation. It is also possible, however, that the connection is possible in different angular positions or is adjustable.

Advantageous developments of the invention result from the claims, the description and the drawings. The advantages of features and of combinations of a plurality of features mentioned at the beginning of the description only serve as examples and may be used alternatively or cumulatively without the necessity of embodiments according to the invention having to obtain these advantages. Without changing the scope of protection as defined by the enclosed claims, the following applies with respect to the disclosure of the original application and the patent: further features may be taken from the drawings, in particular from the illustrated designs and the dimensions of a plurality of components with respect to one another as well as from their relative arrangement and their operative connection. The combination of features of different embodiments of the invention or of features of different claims independent of the chosen references of the claims is also possible, and it is motivated herewith. This also relates to features which are illustrated in separate drawings, or which are mentioned when describing them. These features may also be combined with features of different claims. Furthermore, it is possible that further embodiments of the invention do not have the features mentioned in the claims.

The number of the features mentioned in the claims and in the description is to be understood to cover this exact number and a greater number than the mentioned number without having to explicitly use the adverb "at least". For example, if a spring is mentioned, this is to be understood such that there is exactly one spring or there are two springs or more springs. Additional features may be added to these features, or these features may be the only features of the respective product.

The reference signs contained in the claims are not limiting the extent of the matter protected by the claims. Their sole function is to make the claims easier to understand.

BRIEF DESCRIPTION OF THE DRAWINGS

In the following, the invention is further explained and described with respect to preferred exemplary embodiments illustrated in the drawings.

FIGS. 5, 7, 8, 9, 10 show front views while FIG. 6 shows a spatial view at an angle from the front.

FIG. 19) through the dynamic correction splint according to FIGS. 14, 15 and 19.

DETAILED DESCRIPTION

The figures show a dynamic correction splint 1. The dynamic correction splint 1 can be used on its own. For that purpose it can be arranged only on one-side from the parts of an extremity of the person to be treated with a joint arranged between these parts and then by fixed via straps or other fixing devices. Preferably, however, two such dynamic correction splints or a dynamic correction splint and a follower splint are fixed on opposing sides of the parts of the extremity and the joint. In this case the two dynamic correction splints can also be connected to each other and/or fixed to the parts of the extremity by fixing straps or other fixing means (cp. e.g. DE 199 04 554 B4).

Functionally, a difference is made on the dynamic correction splint 1 between the joint 2 and the two bar-like base bodies 3, 4 connected to each other via the joint 2. The base bodies 3, 4 in use extend in parallel to the extremities. The base bodies 3, 4 serve for transmitting the correction moment onto the extremities and fixing the dynamic correction splint 1 to them. The joint 2 serves for enabling a change of the pivoting angle or bending angle of the dynamic correction splint 1. Into the joint 2, further functions are integrated, especially a setting of the range of the possible pivoting angles of the dynamic correction splint 1, e.g. by stops and/or a worm drive, a spring device for creating the correction moment and measures for influencing the characteristic of the correction moment.

Figure 1:
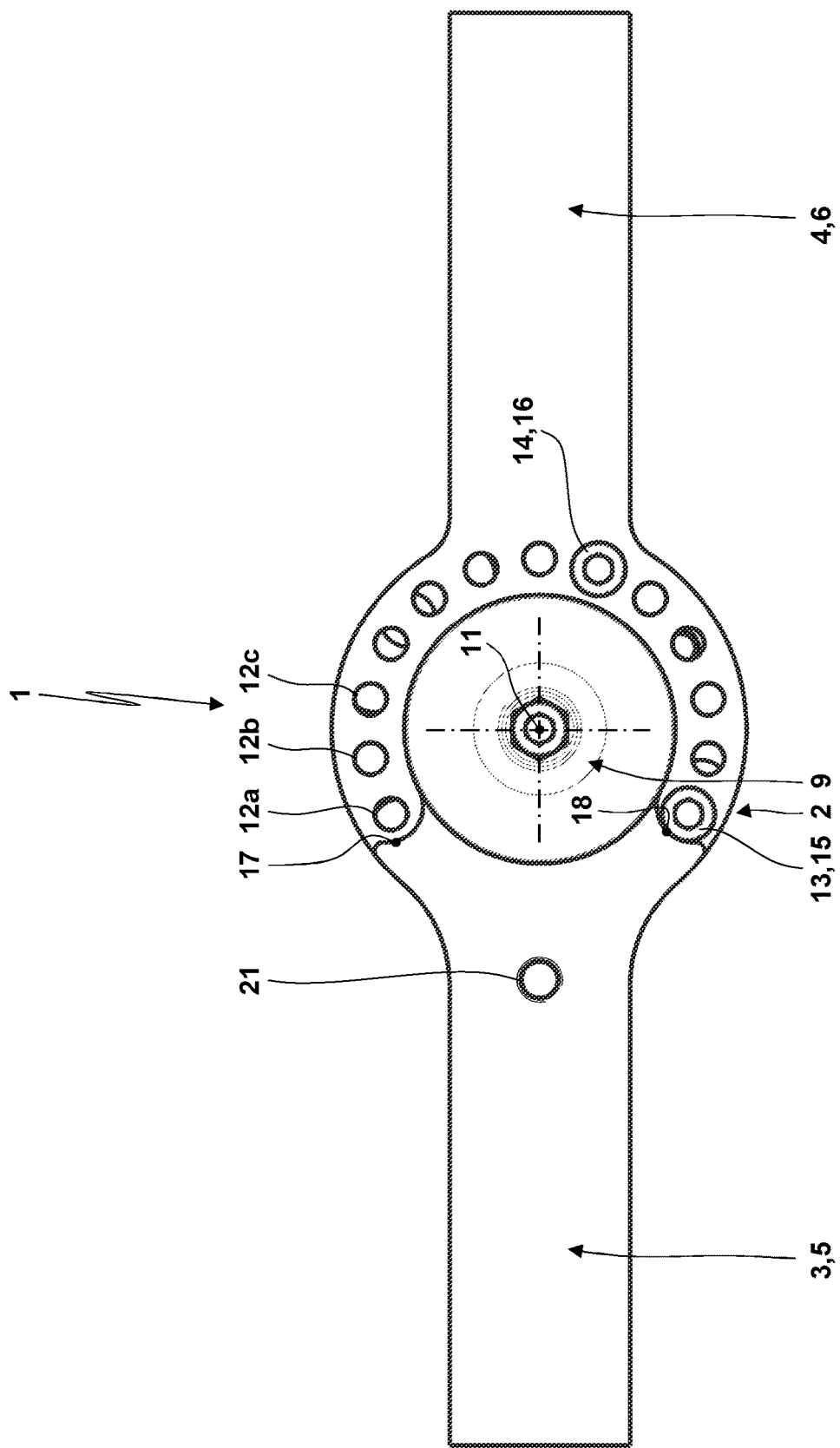
FIG. 1 shows a back view of a dynamic correction splint in a straightened position.

Constructively, the dynamic correction splint 1 is formed with three panel-like construction elements, that is, a splint part 5, a splint part 6 and a supporting body 7 (which is a supporting disc 8 here). The splint part 6 and the splint part 5 in this sequence contact each other in the region of the joint 2, where they can directly contact each other or between them a sliding disc is arranged to reduce the friction during the pivoting movement. The splint parts 5, 6 and the supporting disc 8 each have a central bore. Through the central bore from the back a plate screw 9 extends. On the opposite side the plate screw 9 is connected (especially screwed) to a support 10. The splint parts 5, 6 and the supporting disc 8 (and sliding discs possibly arranged between them) are caught between the head of the plate screw 9 and the support 10 in such a way that they can pivot about a pivoting axis 11 which is vertical to the plane of projection according to FIG. 1.

Figure 9:
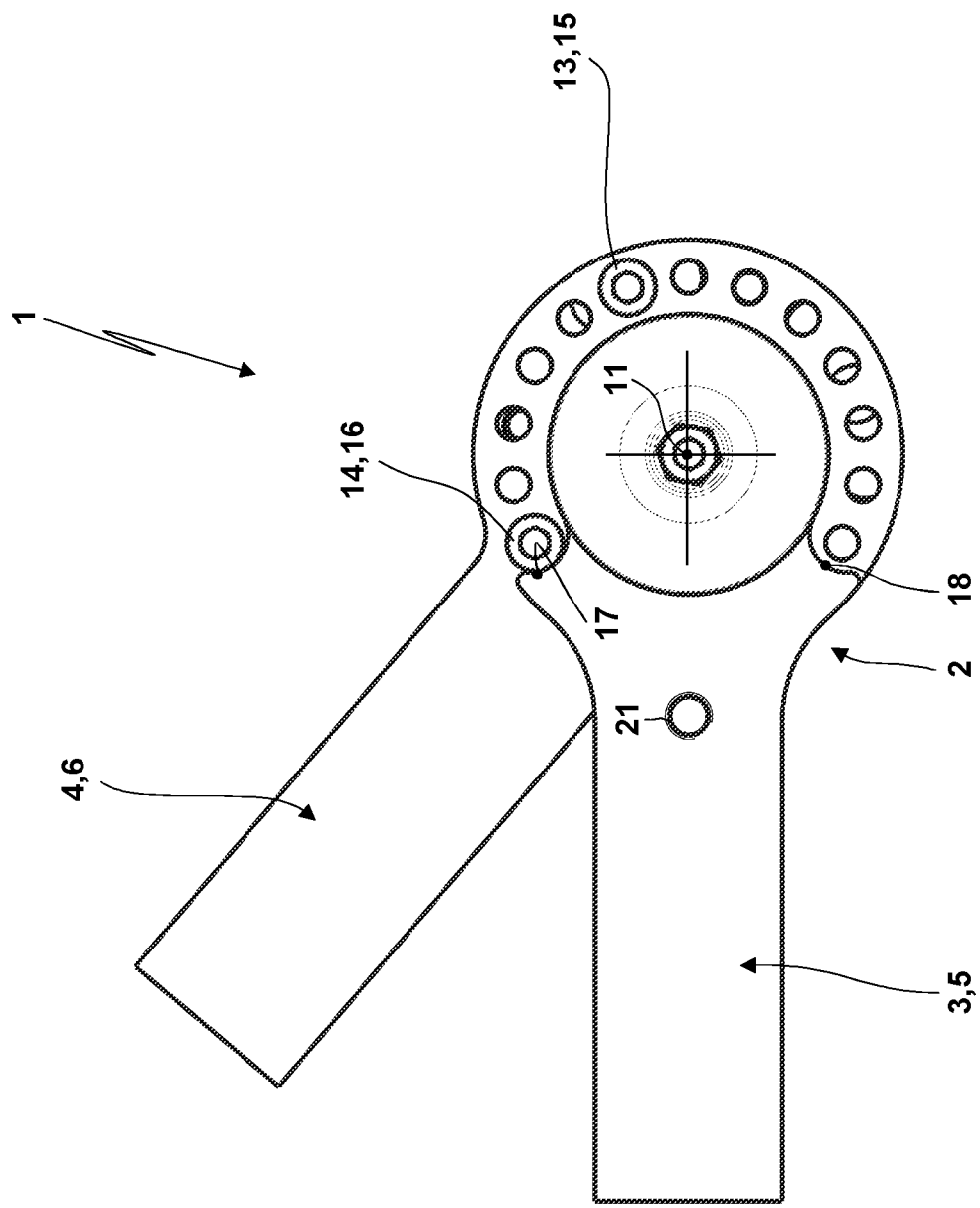

In the region of the joint 2 the splint part 6 has bores 12a, 12b . . . distributed evenly around the circumference. In two bores 12, two stops 13, 14 are fixed. Preferably, the stops 13, 14 are screws 15, 16. The screws 15, 16 comprise a cylinder head with a hexagon socket. The screws 15, 16 can be screwed into the bores 12 comprising a corresponding thread. The stops 13, 14 each serve for limiting the possible pivoting angle of the splint parts 5, 6 in one direction. On the part of its circumference turned towards the splint part 6 the splint part 5 has a radius which is smaller than the distance of the stops 13, 14 from the pivoting axis 11. This design serves for avoiding a collision of the stops 13, 14 with the splint part 5. The part of the circumference with the smaller radius is on both sides limited by counter-stops 17, 18 which are formed here by rounded radial extensions of the splint part 5 (in FIG. 1: in an eleven o'clock position and in a seven o'clock position with respect to the pivoting axis 11). In the straightened position shown in FIG. 1, the stop 13 rests against the counter-stop 18. In this way it is avoided that in FIG. 1 (when the splint part 5 is fixed) the splint part 6 is pivoted past the straightened position in a clockwise direction. On the contrary, a pivoting of the splint part 6 in an anti-clockwise direction is possible until the stop 14 contacts the counter-stop 17. In this way the maximum bending angle is set (cp. FIG. 9). The minimum and maximum bending angle are set by the circumferential position of the stops 13, 14 (as well as the circumferential position of the counter-stops 17, 18). By choosing two of the bores 12 for fixing the stops 13, 14 the minimum bending angle, the maximum bending angle and the possible pivoting range of the splint parts 5, 6 can be set.

Figure 2:
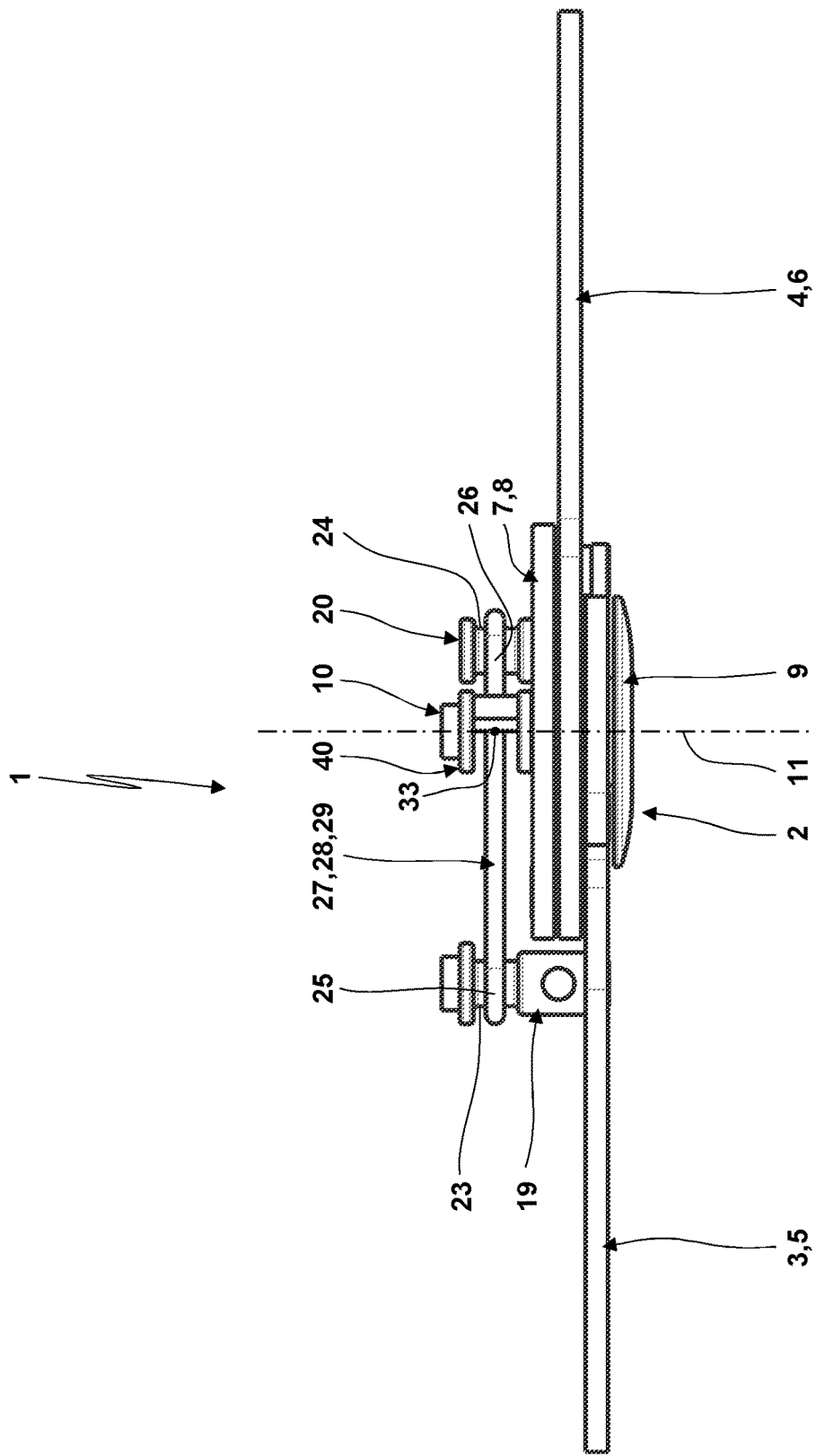
FIG. 2 shows the dynamic correction splint according to FIG. 1 in a side view.
Figure 3:
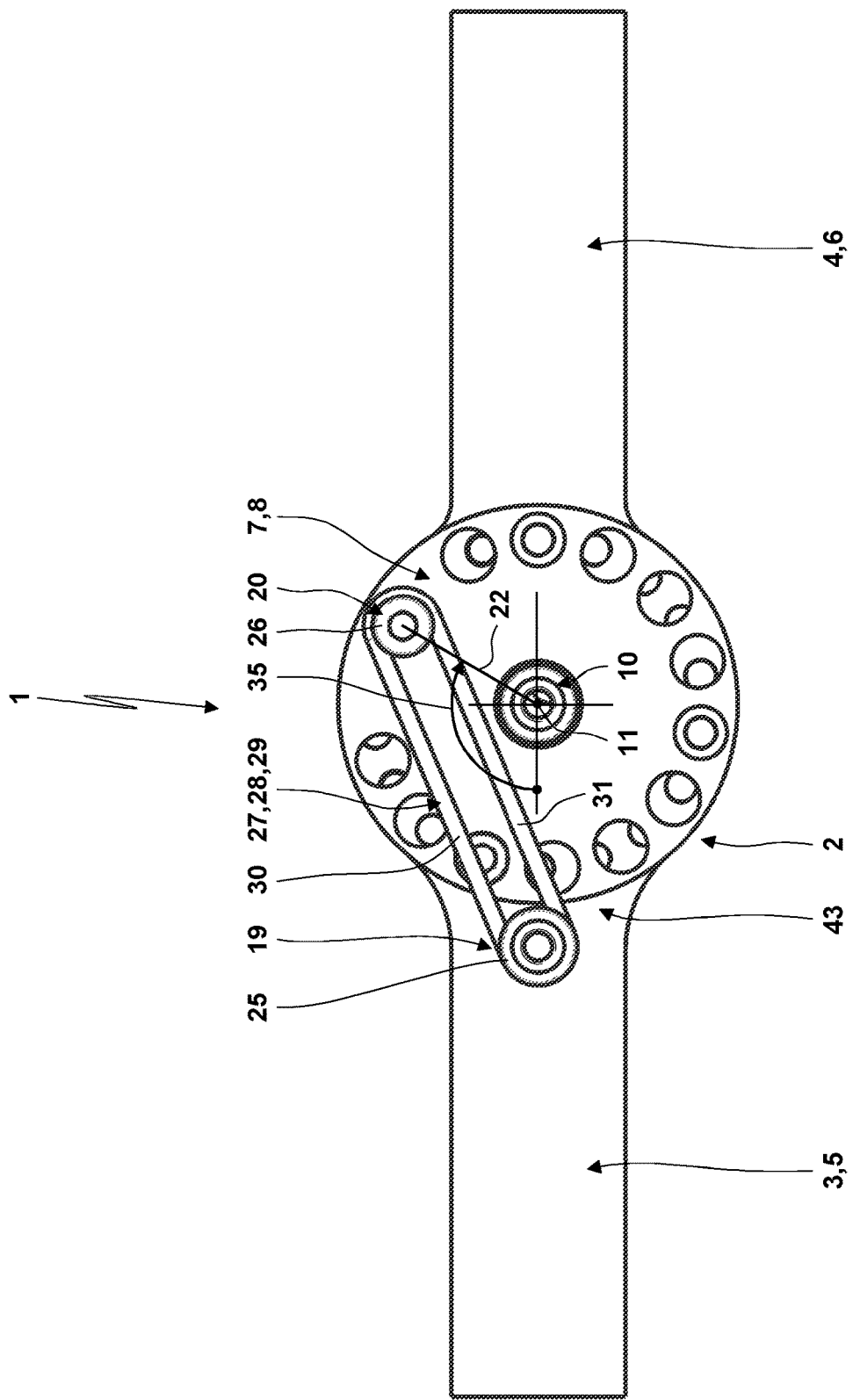
FIG. 3 shows the dynamic correction splint according to FIGS. 1 and 2 in a front view.

In FIGS. 2 and 3, it can be seen that on the supporting disc 8 and on the splint part 5 each a supporting bolt 19 is fixed, which here for example is achieved by screwing a thread of the supporting bolts 19, 20 into corresponding threaded bores of the splint part 5 and the supporting disc 8. For the embodiment shown, the threaded bore 21 for the supporting bolt 19 is located on the longitudinal axis of the splint part 5 in a transition region from the joint 2 to the base body 3. In FIG. 3 it can be seen that the supporting bolt 20 is held on the supporting disc 8 with an eccentricity or a radius 22 with respect to the pivoting axis 11. The supporting bolts 19, 20 preferably comprise a hexagon socket contact surface, which enables the screwing of the supporting bolts 19, 20 into the splint part 5 or the supporting disc 8. The supporting bolts 19, 20 each have a groove 23, 24. The supporting bolts 19, 20 are arranged in parallel to the pivoting axis 11 and extend on the front face of the dynamic correction splint 1. Spring bases 25, 26 of a spring device 27 are linked to the supporting body 19, 20 and therefore to the splint part 5 and the supporting disc 8. For the embodiment shown, the spring device 27 is realized as a tension spring 28, here in a realization as a continuous elastic band 29. The elastic band 29 is hooked into the grooves 23, 24 of the supporting bolts 19, 20 in a pre-tensioned way. The elastic band 29 forms two pre-tensioned band parts 30, 31 between the supporting bolts 19, 20. Both band parts 30, 31 create a partial spring force, which with respect to the pivoting axis 11 can comprise a partial lever arm and therefore create a partial correction moment on the dynamic correction splint 1. As a simplification, in the following it will be referred to a spring force caused together by the two band parts 30, 31 with a corresponding spring arm. The correction moment resulting from the spring force in the straightened position of the dynamic correction splint according to FIGS. 1 to 4 has the effect that the stop 13 is pulled against the counter-stop 18, in which way the straightened position is secured. A leaving of the straightened position with an increase of the bending angle necessitates that a bending moment has to be exerted onto the splint parts 5, 6 by the user to reduce the contact force between the stop 13 and the counter-stop 18 and then move the stop 13 away from the counter-stop 18. This bending out of the straightened position according to FIG. 3 into a bended position according to FIG. 5 leads to the result that the supporting bolt 20 moves around the pivoting axis 11 in a clockwise direction, in which way the distance of the supporting bolts 19, 20 increases and therefore the spring force of the tension spring 28 increases. At the same time, however, the lever arm of the tension spring 28 with respect to the pivoting axis 11 decreases.

The supporting disc 8 is rigidly connected to the splint part 6. It is possible that the rigid connection can be provided in different angular positions for adjusting the dynamic correction splint 1. In this way an adjustability is provided. For an adjustment the supporting bolt 20 can be mounted to the supporting disc 8 in different circumferential positions and/or a continuous adjustment of the relative position of the supporting disc 8 is possible via a worm drive.

In the straightened position according to FIGS. 1 to 4 and for small bending angles 32 (cp. FIG. 5), the spring device 27 is only linked with the spring bases 25, 26 to the supporting bolts 19, 20 or the splint part 5 and the supporting disc 8. Especially, there is no interaction in the form of a contact with the support 10. This pure linkage by the spring bases is here also referred to as "a first coupling 43".

Figure 4:
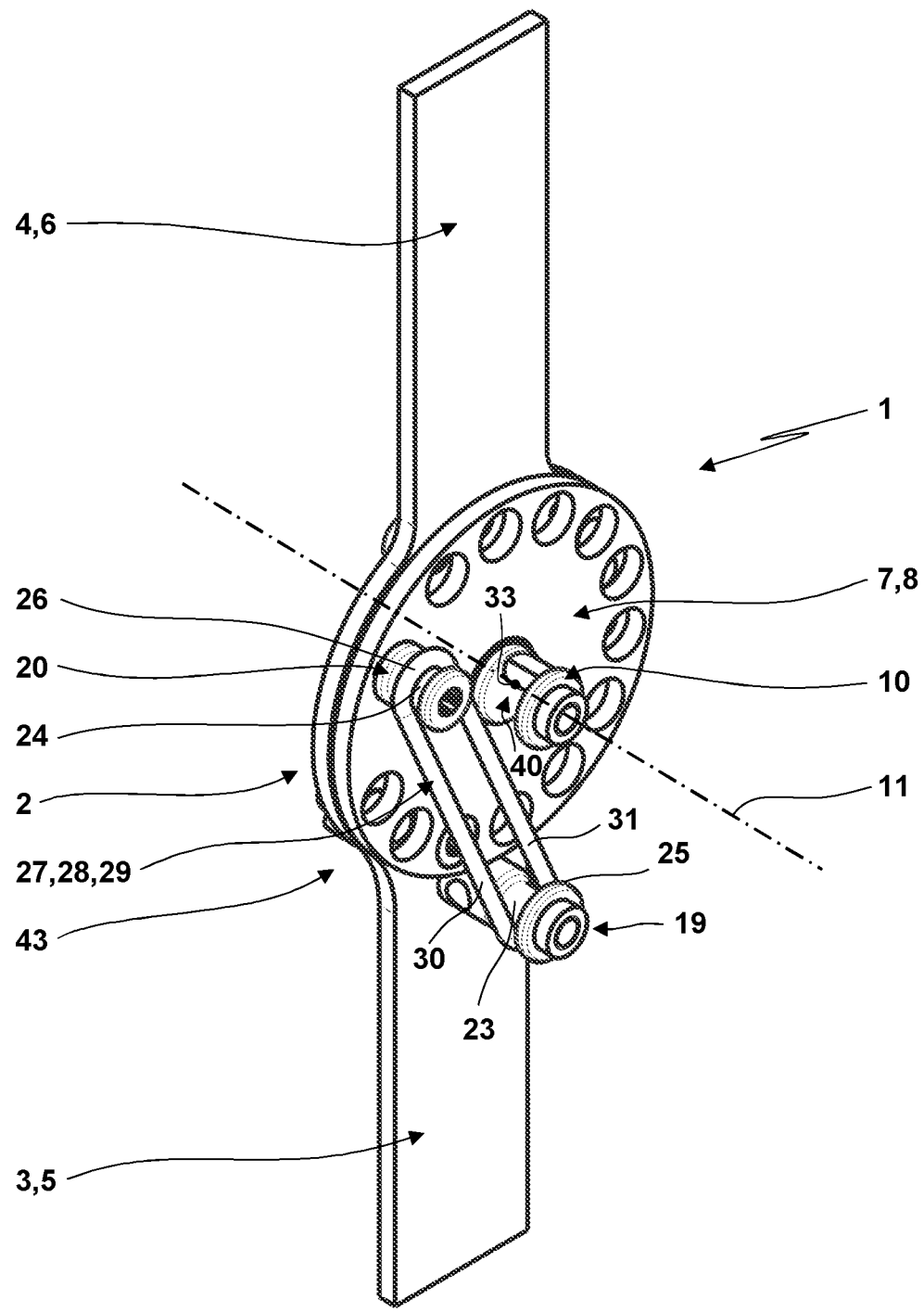
FIG. 4 shows the dynamic correction splint according to FIGS. 1 to 3 in a spatial view at an angle from the front.
Figure 5:
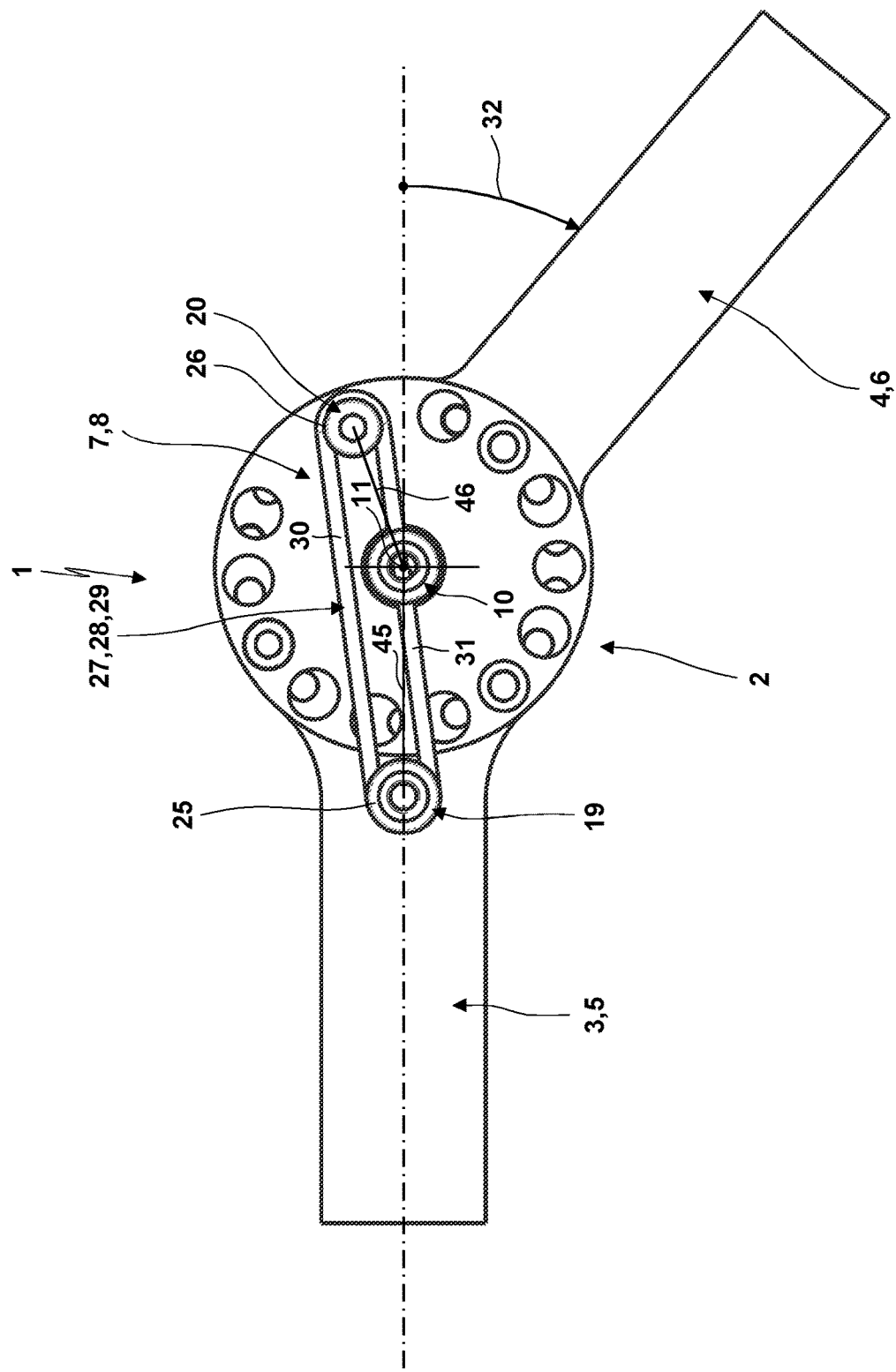
FIGS. 5 to 10 show the dynamic correction splint according to FIGS. 1 to 4 in different bending positions, where
Figure 6:
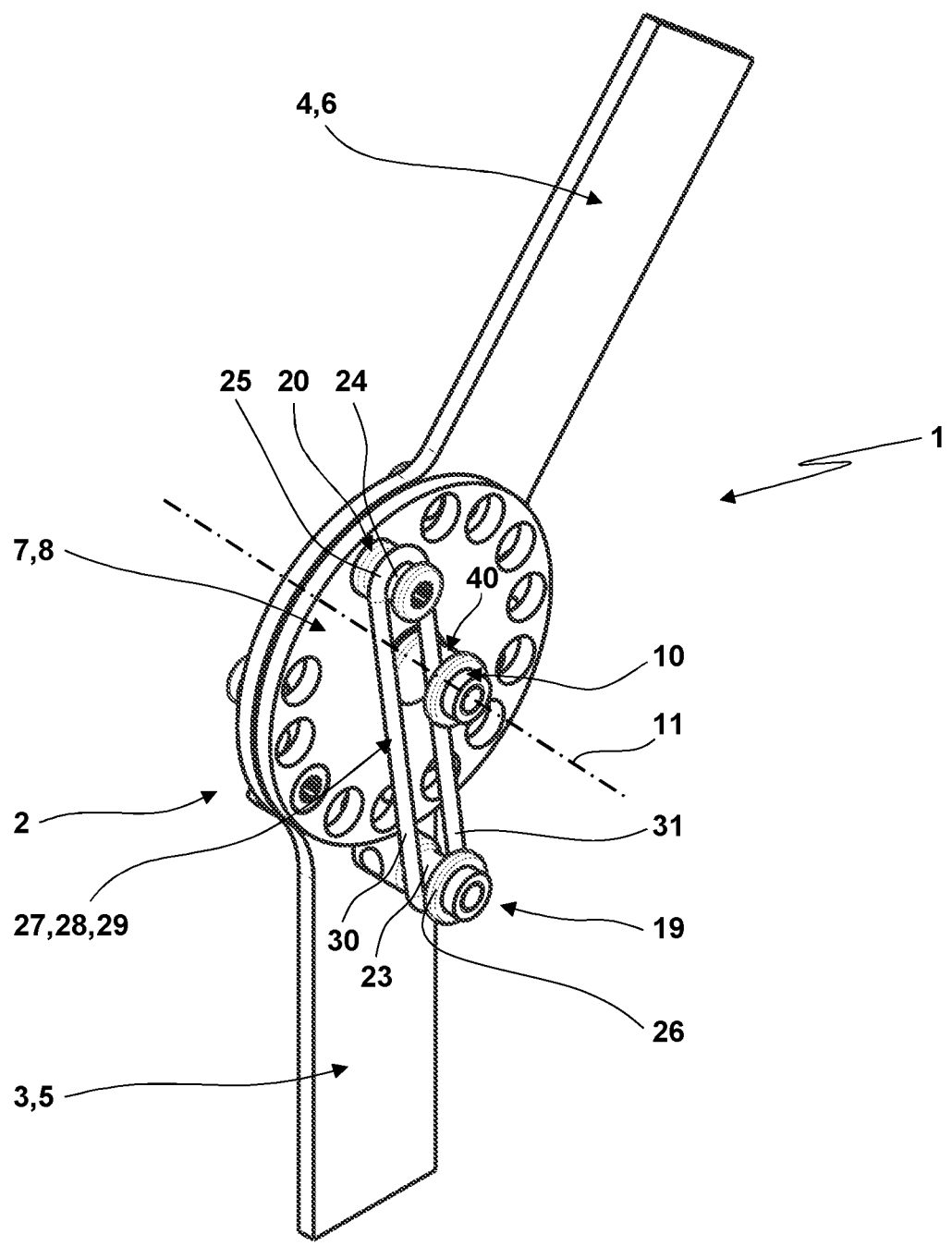

As can especially be seen from the spatial view according to FIG. 4, the support 10 is realized with an eccentricity or a crank-like partial region in the plane of motion of the spring device 27. The eccentricity or the offset of the crank-like partial region is dimensioned in such a way that the support 10 forms a support surface 33 through which the pivoting axis 11 extends. For the bending angle 32 according to FIG. 5 (which here is approximately 45°), the band part 31 has already come to rest against the support surface 33. The partial spring force of the band part 31 therefore runs through the pivoting axis 11 which results in the band part 31 not creating a partial correction force. However, the other band part 30 still has a small lever arm with respect to the pivoting axis 11 so that the partial spring force of this band part 30 creates a correction moment (which is reduced when compared to the correction moment in the straightened position according to FIGS. 1 to 4).

Figure 7:
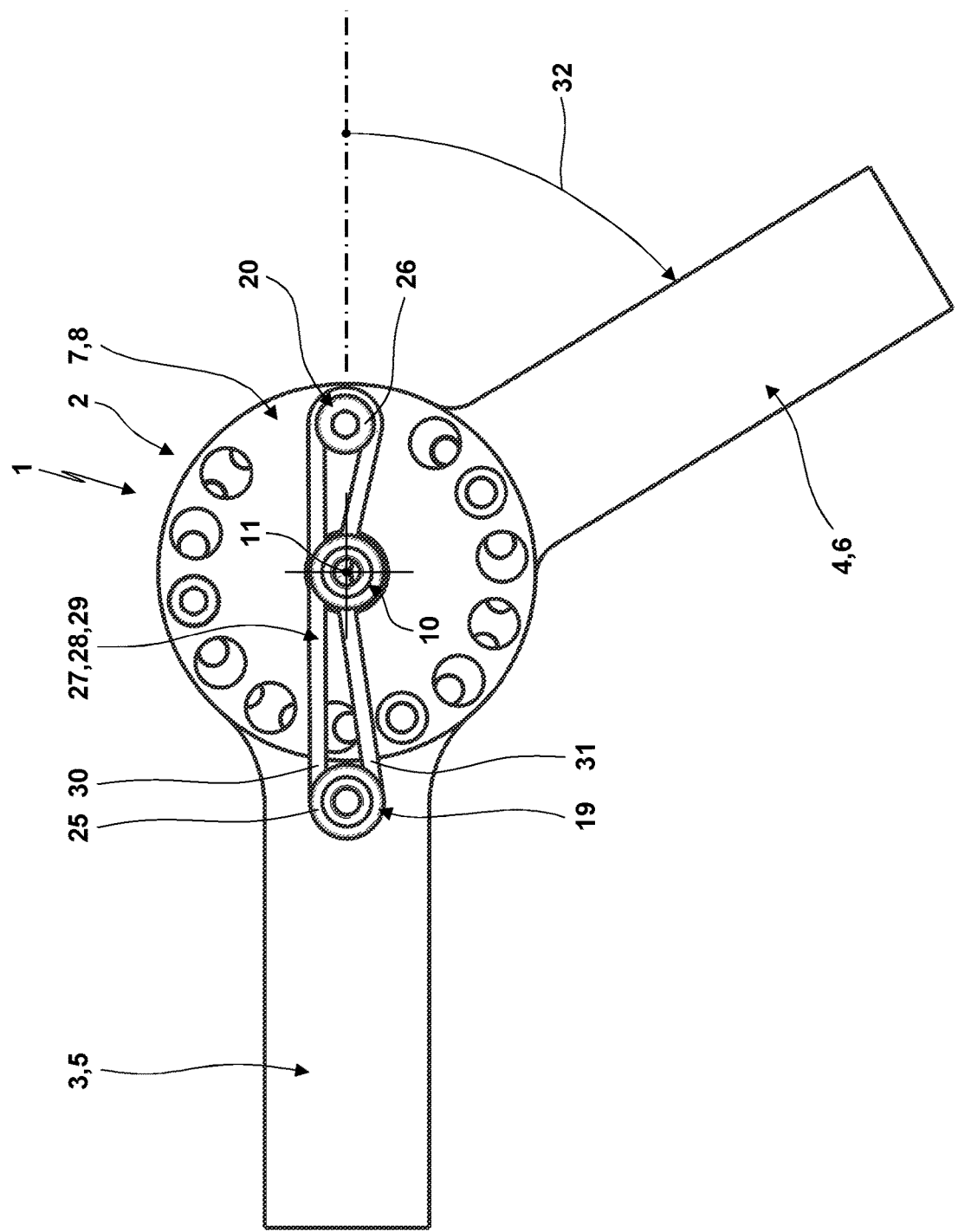
Figure 8:
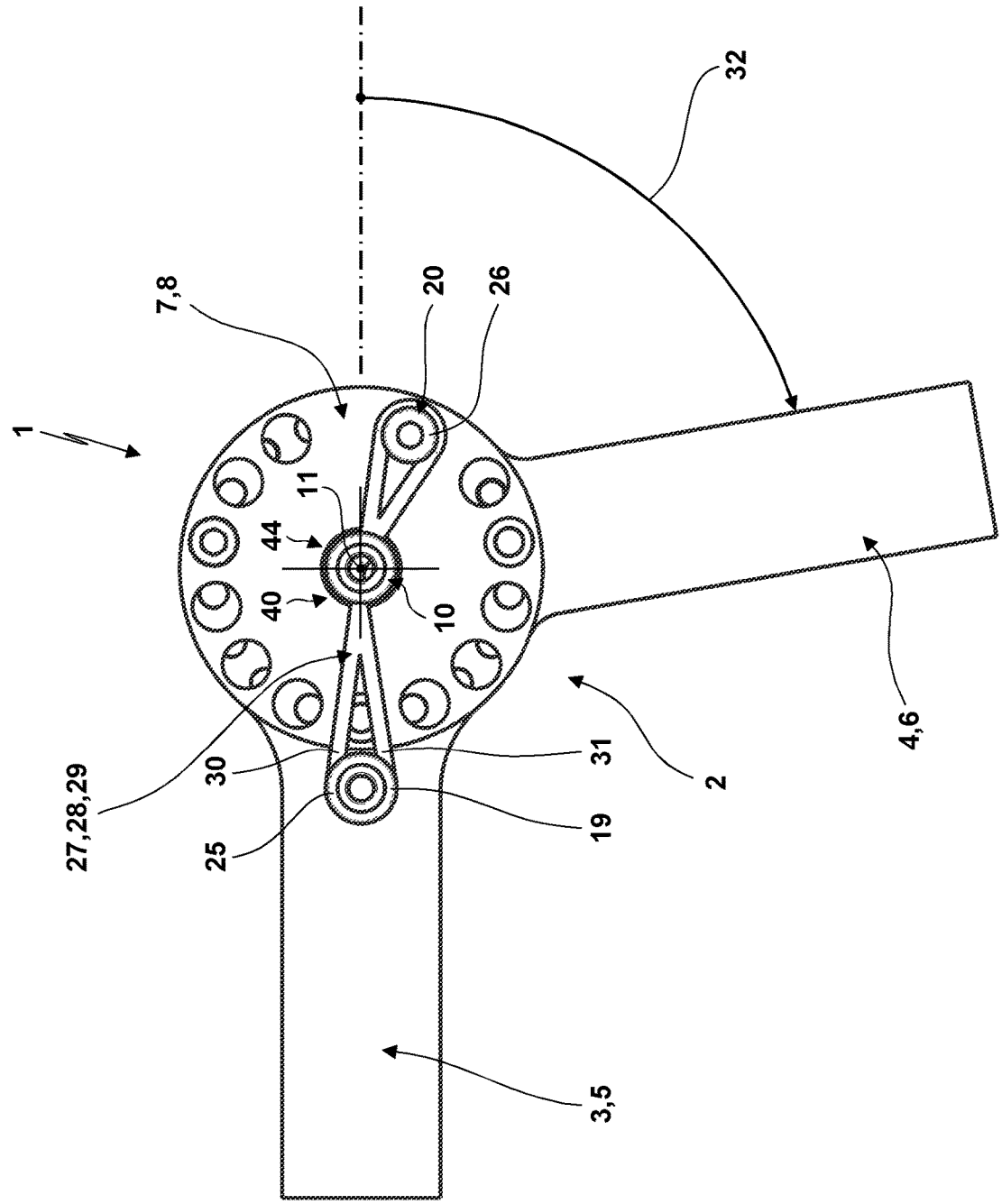
Figure 10:
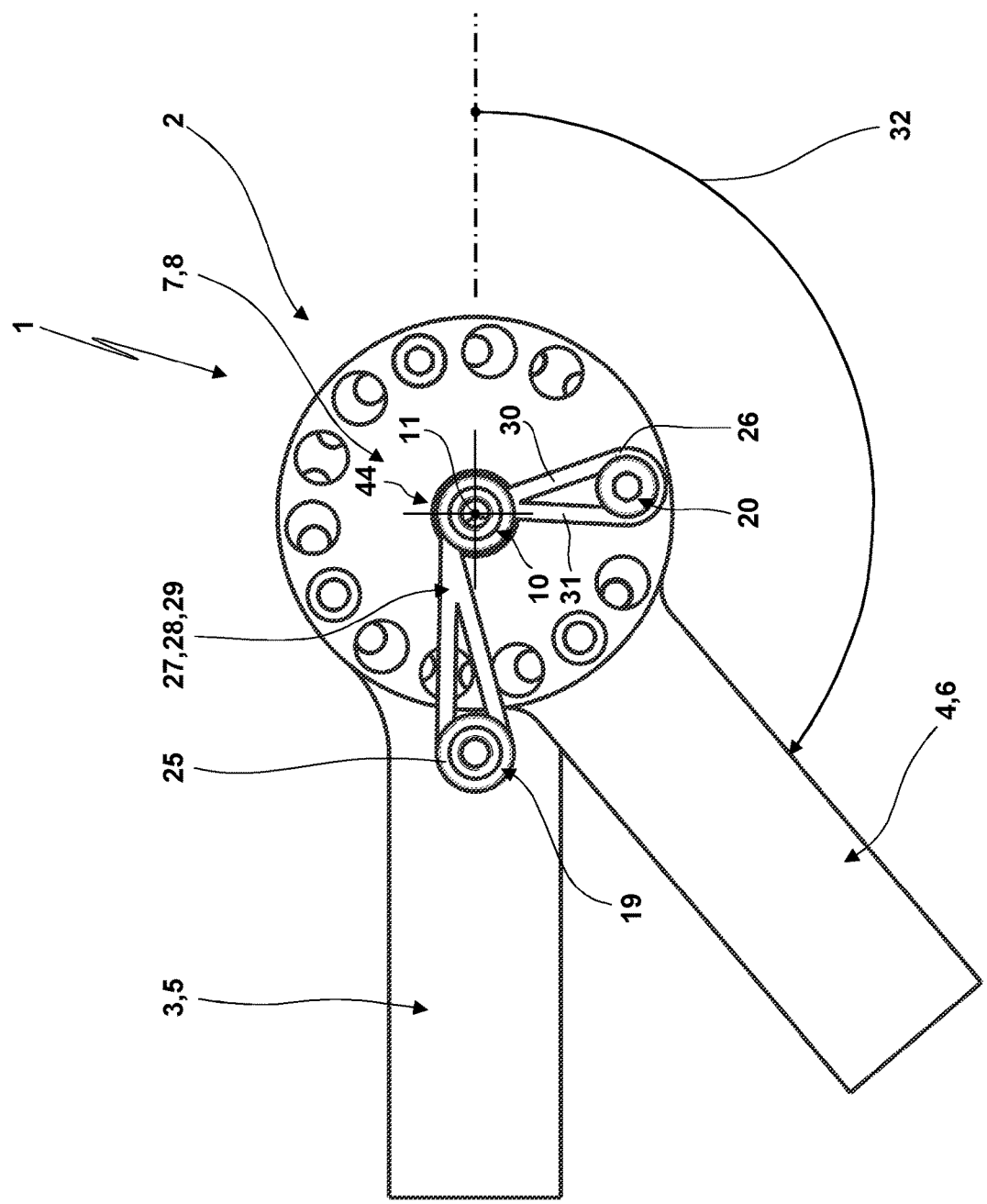

With a further increase of the bending angle 32 according to FIGS. 7 and 8 both band parts 30, 31 come to rest against the support surface 33. This results in the spring device 27 not being able to produce a correction moment independently of the spring force in the spring device 27. the reason is that the spring force of the spring device 27 does not have a lever arm with respect to the pivoting axis 11 of the splint parts 5, 6. For a further increase of the bending angle 32, therefore no application of a moment by the wearer of the dynamic correction splint 1 will be required. In this way then a pivoting up to the maximum bending angle 32 according to FIG. 10 is possible, where the maximum bending angle 32 is set by the stop 14 coming to rest against the counter-stop 17 (cp. FIG. 9).

Figure 11:
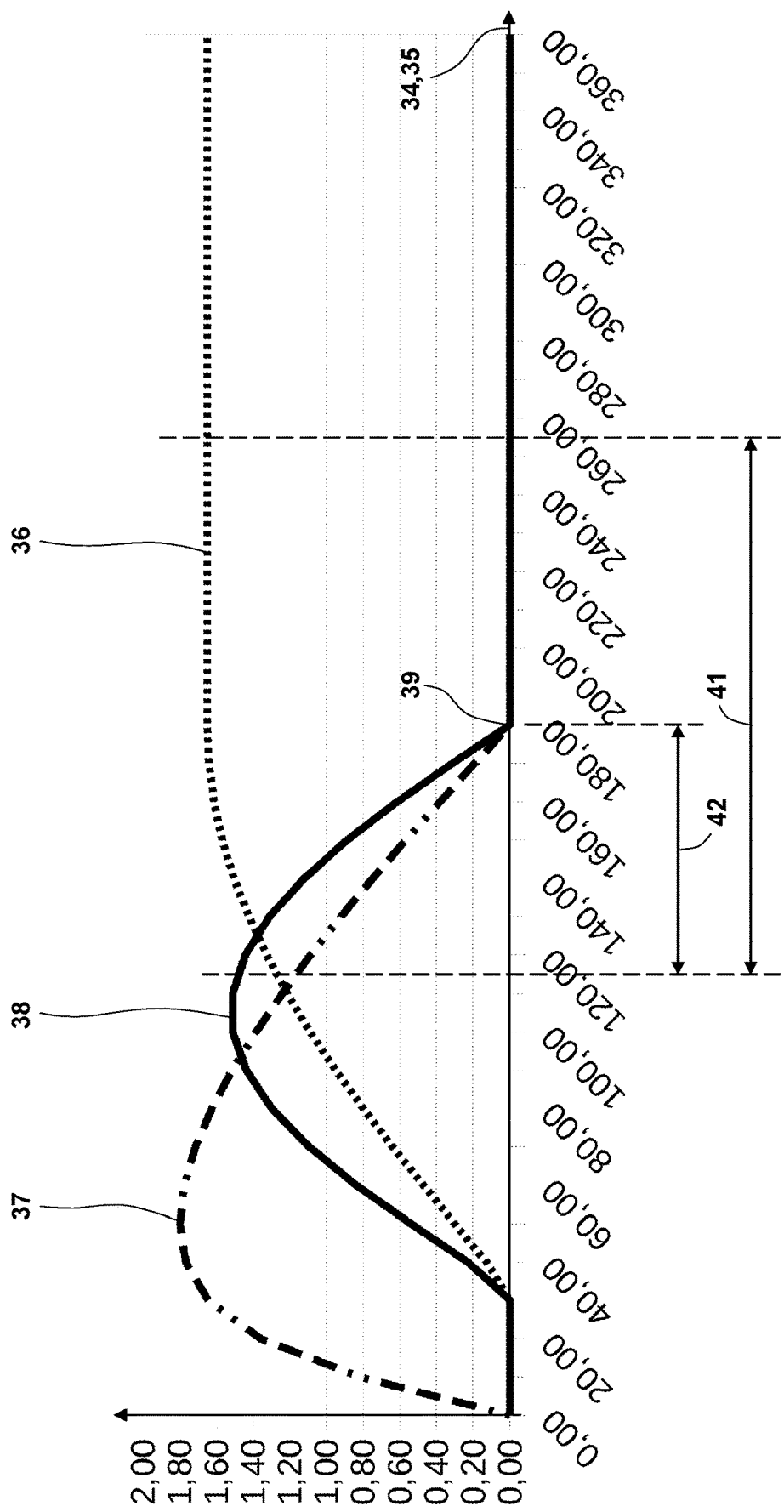
FIG. 11 shows characteristics of a lever arm, a spring force and a correction moment in dependence on the pivoting angle of splint parts of the dynamic correction splint according to FIGS. 1 to 10.

FIG. 11 shows the kinematic relationships or characteristic for a dynamic correction splint according to FIGS. 1 to 10. On the abscissa 34, the angle 35 is shown under which the supporting bolt 20 and therefore the spring base 26 of the spring device 27 are arranged relative to a possible starting position, here a nine o'clock position in FIG. 3. The theoretic variation of this angle 35 in the shown angular range of 0° to 360° for the depiction of the kinematic relationships necessitates that the stops 13, 14 are considered to be removed. Plotted against the angle 35 in FIG. 11 are the spring force of the spring device 27 with the dotted curve 36, 37, the lever arm of a possible spring force of the spring device 27 with the dash-dotted curve and the correction moment resulting from the product of the spring force and the lever arm with the continuous curve 38. The curve 38 of the correction moment here is also referred to as the "characteristic" of the correction moment. On the y axis the lever arm is given in centimeters while the spring tension is given in units of 100 N and the correction moment in Nm. Without a limitation of the invention to this being intended, a dynamic correction splint according to the invention can comprise a lever arm, a spring tension and a correction moment corresponding to the curves 36, 37, 38 shown (or with curves which differ with respect to the curves 36, 37, 38 shown by ±20% or ±10% or 5%).

When the angle 35 is 180°, a transition 39 is reached for which the spring device 27 comes to rest against the support surface 33, in which way for the range of the angle 35 from 180° to 360° the curve of the lever arm 37 is zero. On the contrary, the curve of the lever arm 37 for the range of the angle 35 from 0° to 180° can be calculated in dependence on the angle relations under use of trigonometric functions. The length of the spring device 27 or the tension spring 28 here is chosen in such a way that the spring device 27 in the range of the angle 35 from 0° to 30° is not yet tensioned so that here the curve 36 is zero. Only for an angle 35 larger than 30°, the spring device 27 is tensioned. Even when assuming a linear spring characteristic of the spring device 27, due to the angle relations in the range from 30° to 180° of the angle 35 a non-linear but continuous increase of the spring force of the spring device 27 results which is proportional to the angle-dependent distance of the two spring bases 25, 26. If for the angular range from 180° to 360° the spring device 27 rest against the support surface 33, with the pivoting of the splint parts 5, 6 the distance of the spring bases 25, 26 does not change so that the curve 36 of the spring force constantly corresponds to the maximum reached for the angle of 180°. From the product of the spring force according to curve 36 with the lever arm according to curve 37, then the curve of the correction moment 38 results. Due to the chosen angular relations, in the angular range from 30° to 180° the correction moment acts towards a reduction of the angle 35.

In the shown characteristic the curve 38 of the correction moment comprises a kink at the transition 39. The kink in the region of the transition 39 and a correction moment of zero in the angular range from 180° to 360° are caused by a switching mechanism 40. The switching mechanism 40 bases on providing different boundary conditions of the spring device 27 in a motion-controlled way and in dependency on the angle 35 or the bending angle 32:

a) In a first switching state for angle ranges before reaching the transition 39, the spring device 27 is connected only with its spring bases 25, 26 to the splint part 5 on the one hand and the splint part 6 on the other hand, here with the supporting disc 8, which is also called the first coupling 43. A change in the angle 35 or the bending angle 32 leads to a change in the distance of the spring bases 25, 26, so that in dependence on the change of the angle also an altered spring force in the spring device 27 results.

b) If, on the contrary, the spring device 27 comes to rest against the support surface 33 of the support 10 in a motion-controlled way by the change of the angle 35 or the bending angle 32, the motion-controlled switching of the switching mechanism 40 to the second switching state occurs. After the actuation of the switching mechanism 40 and after the transition 39 there is an additional boundary condition of the spring device 27. As a consequence, for any angle 35 in the angle range from 180° to 360° and for a corresponding bending angle 32 the spring device 27 rests against the support surface 33. This is also referred to as the second coupling 44 here. The change of the angle then, however, does not result in a change of the distance of the spring bases 25, 26, a change of the extension of the spring device 27 or a change of the spring force 36. Furthermore, for this angular range the lever arm 37 of the spring force 36 is zero, which means that also the correction moment is zero.

Figure 12:
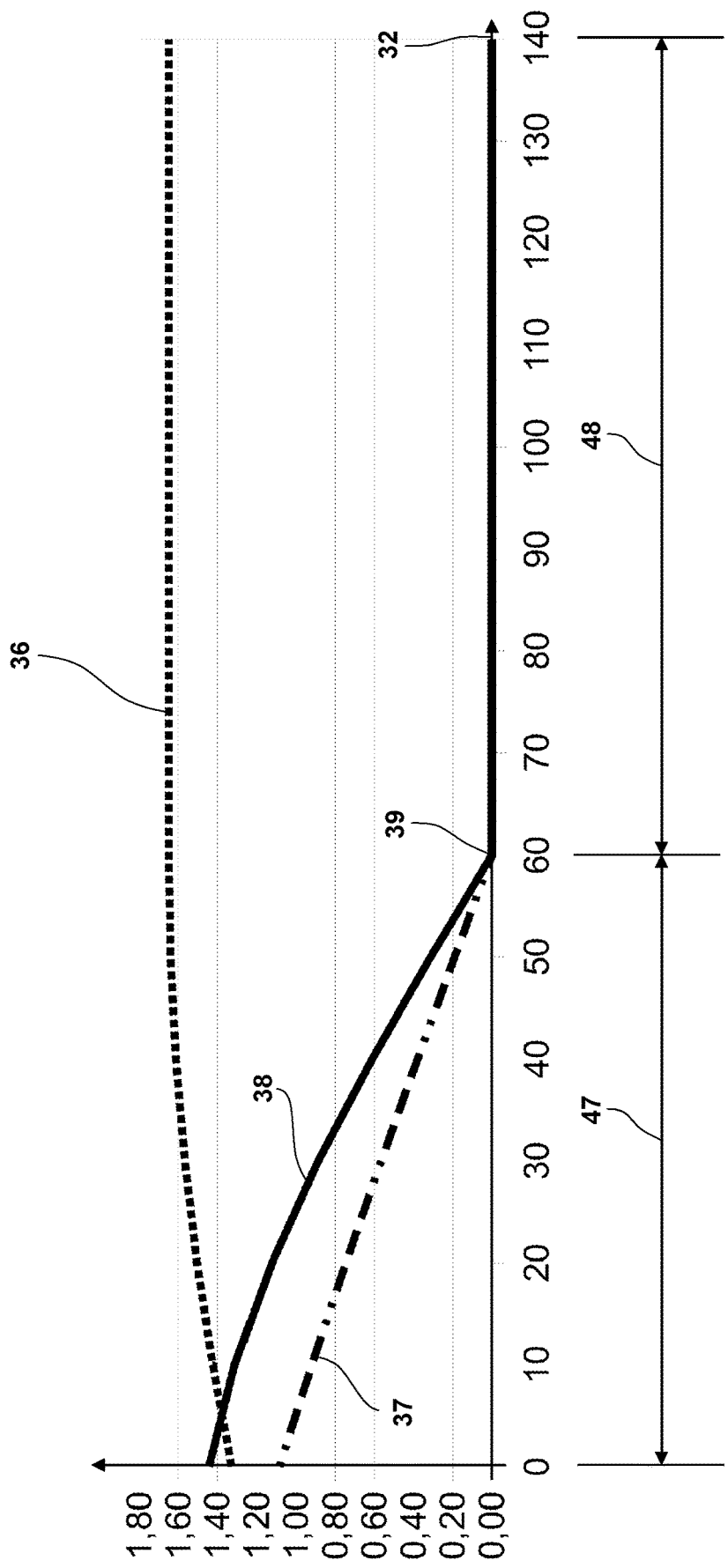
FIGS. 12 and 13 show selected characteristics of the curves according to FIG. 11 for different uses, designs and adjustments of the dynamic correction splint according to FIGS. 1 to 10.

The characteristic of the correction moment according to FIG. 11 can be used in a different way depending on the individual area of application. An adjustment of the used portion of the characteristic is done by the choice of the circumferential position of the supporting bolt 20 and therefore the spring base 26 in the straightened position. If, for example, the supporting bolt 20 is mounted onto the supporting disc 8 in the nine o'clock position in the straightened position, the increase of the bending angle 32 causes the initial portion of the characteristic of the correction moment according to FIG. 11 to be run through, starting from the angle 35 of zero. For the embodiment shown in FIGS. 1 to 10, the straightened position approximately corresponds to an angle 35 in FIG. 11 of 120° (cp. the angle 35 in FIG. 3), while for the maximum bending angle 32 according to FIG. 10 the angle 35 corresponds to approximately 260°. The range of the characteristic of the correction moment run through by the dynamic correction splint according to FIGS. 1 to 10 is in FIG. 11 marked with reference sign 41. This section of the characteristic with the corresponding spring force and the lever arm is again shown in FIG. 12, where here as the abscissa not the angle 35 has been chosen, but the bending angle 32 according to FIGS. 1 to 10. Such a range of the bending angle 32 can for example be used at a use of the dynamic correction splint 1 for an elbow joint or a knee joint. It can be seen in FIG. 12 that in a first pivoting range 47 the correction moment is created while in a second pivoting range 48 no correction moment is created. The transition from the first pivoting range 47 to the second pivoting range 48 is achieved via the transition 39.

Figure 13:
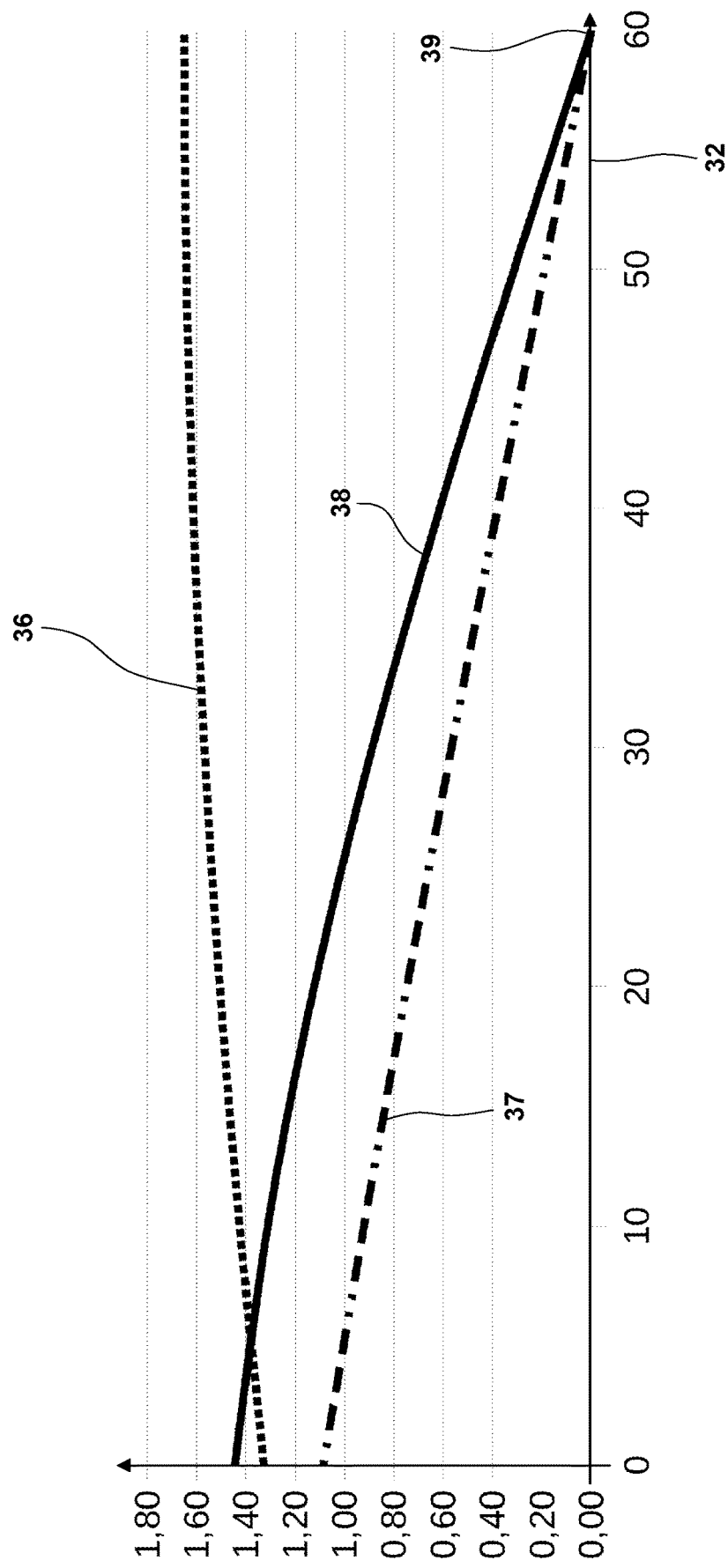

For another area of application, another portion 42 of the characteristic of the correction moment can be used. FIG. 13 shows a portion 42 of the characteristic of the correction moment in the range of the angle 35 of 120° to 180°, which corresponds to a bending angle 32 of 0° to 60°. It can be seen that in the use of the dynamic correction splint 1 the transition 39 with an actuation of the switching mechanism 40 is not necessarily used. From the characteristics of the correction moment according to FIGS. 12 and 13 it can be taken, however, that in the correction position, which here corresponds to the straightened position with a bending angle 32 of zero, the correction moment has an absolute maximum and that with an increase of the bending angle 32 the correction moment decreases continuously. The correction moment according to FIG. 13 goes to zero without a kink while according to FIG. 12 there is a kink in the region of the transition 39. A corresponding use of the same dynamic correction splint 1 with the same characteristic is possible if there is to be a correction effect for a flexion, for which the correction position is not the straightened position but a maximum bent position. In this case, too, the correction moment is at its maximum in the correction position, which here is the maximum bending position, with the corresponding curves with a decrease of the bending angles.

Before the transition 39 or before the actuation of the switching mechanism 40, a coupling 43 of the spring device 27 to the two splint parts 5, 6 is only provided by the linking of the spring bases 25, 26 to the switching mechanism 40. On the contrary, after the transition 39 or after the actuation of the switching mechanism 40, a coupling 44 of the spring device is provided both by the linking of the spring bases 25, 26 to the splint parts 5, 6 as well as by the contact of the spring device 27 with the support surface 33 of the support 10.

In FIG. 5, in can furthermore be seen that the connecting axes 45, 46 of the supporting bolt 19 or the spring base 25 with the pivoting axis 11 on the one hand and of the pivoting axis 11 with the supporting bolt 20 or the spring base 26 on the other hand form an angle smaller than 180° while the longitudinal axes of the splint parts 5, 6 form an angle larger than 180°. Accordingly, before the actuation of the switching mechanism 40 the correction moment has a direction for decreasing the bending angle 32 and therefore causing a correction moment towards the correction position.

For the embodiment of the dynamic correction splint 1 shown in FIGS. 1 to 10, the supporting disc 8 (for a chosen setting) was fixedly connected to the splint parts 6 so that the spring bases 25, 26 at a change of the bending angle 32 each did not change their relative position on the splint parts 5, 6. The switching mechanism 40 was formed between the spring bases 25, 26 by forming an additional contact surface with the support surface 33.

In FIGS. 14 to 28, another embodiment of a dynamic correction splint 1 is shown in which the spring bases 25, 26 of the spring device 27 are also permanently linked to the splint part 5 on the one hand and the supporting disc 8 on the other hand. However, here no support surface 33 is used for providing the switching mechanism 40. Rather than that, the switching mechanism 40 removes the fixed coupling between the supporting disc 8 and the splint part 6.

Figure 16:
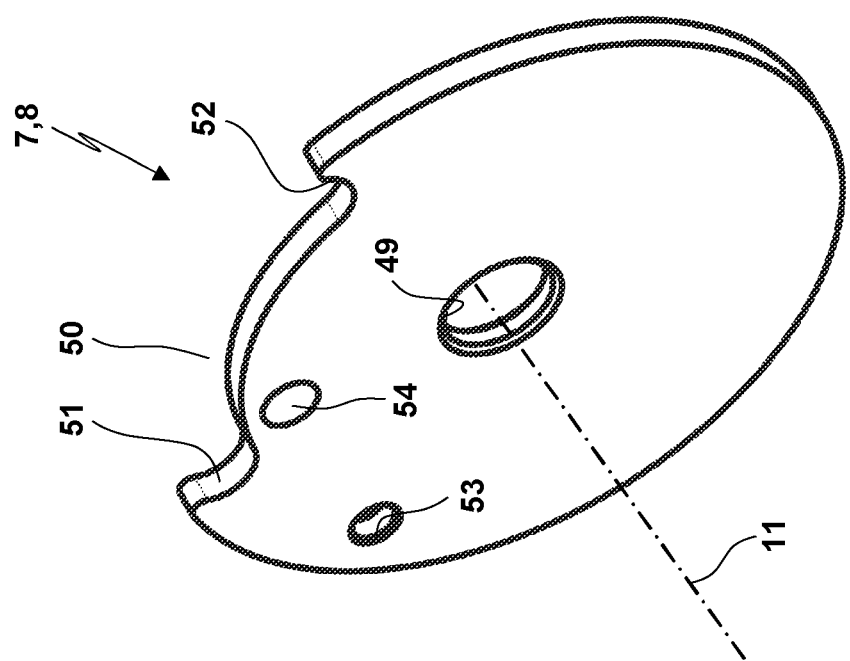
FIG. 16 shows a supporting disc which is employed in a dynamic correction splint according to FIGS. 14 and 15.

FIG. 16 shows the supporting disc 8 as a single part. It has a center bore 49 through which the plate screw 9 can extend and which defines the pivoting axis 11. Furthermore, the generally circular supporting disc 8 comprises a circumferential recess 50 with a reduced diameter which is limited by the counter-stops 51, 52 in the circumferential direction. The supporting bolt 20 is screwed into a threaded bore 53. Finally, radially on the inner side from the circumferential recess 50 the supporting disc 8 comprises a bottom closed recess 54 which has especially a semi-spherical shape or the shape of a part of a sphere.

Figure 17:
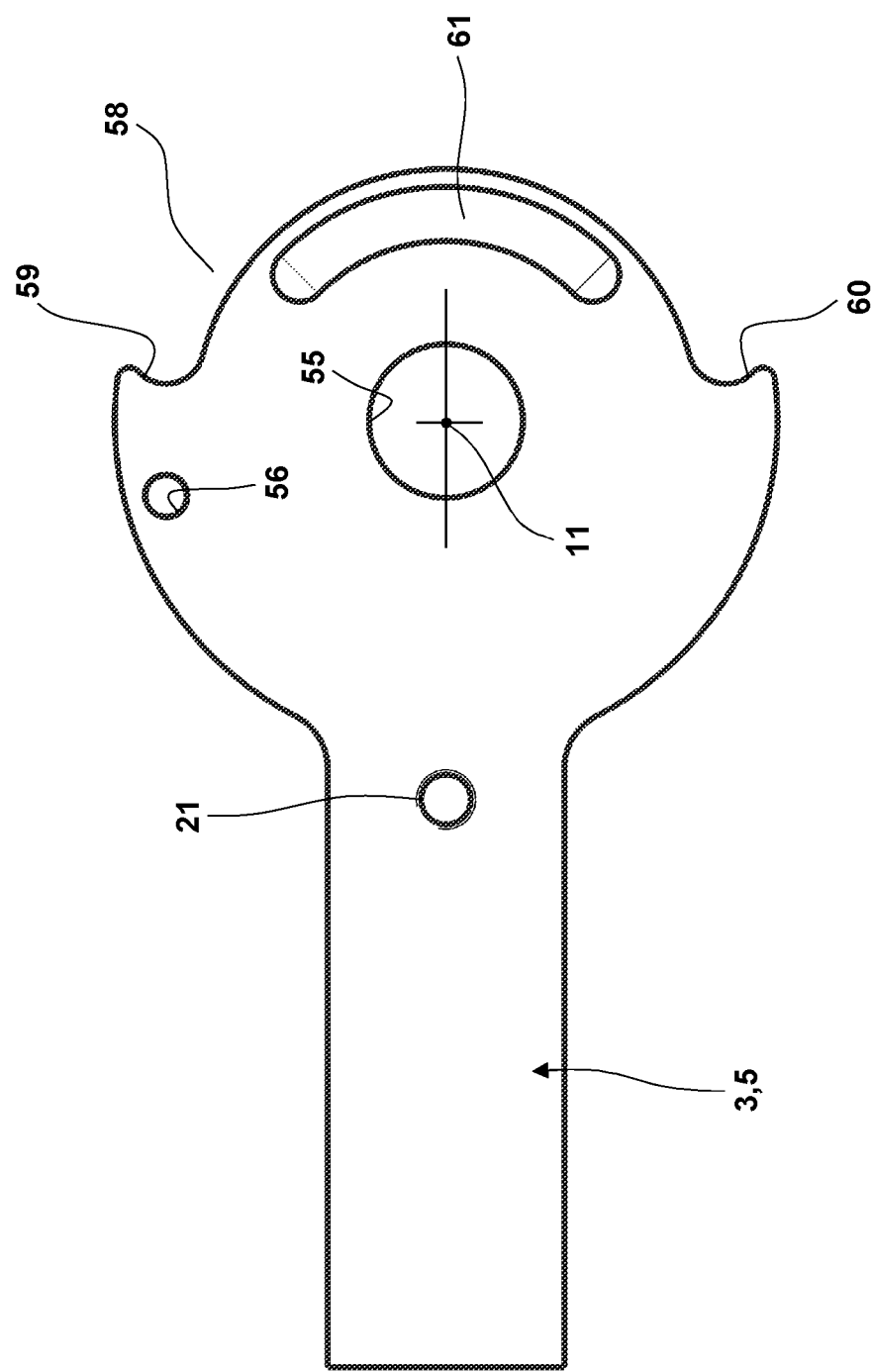
FIGS. 17 and 18 each show a splint part of a dynamic correction splint according to FIGS. 14 and 15.

In the single-part drawing according to FIG. 17 it can be seen that in the region of the joint 2 and next to the threaded bore 21 the splint part 5 has a bore 55 through which the plate screw 9 can extend and which defines the pivoting axis 11. Furthermore, the splint part 5 has a bore or a threaded bore 56 where a stop 57 can be fixed. While generally in the region of the joint 2 the splint part 5 is realized in the shape of a circular plate, it, too, on the side turned away from the base body 3 has a circumferential recess 58 with a reduced radius. In both circumferential directions the recess 58 is limited by counter-stops 59, 60. Finally, on the radially inner side of the circumferential recess 58 the splint part 5 comprises a circumferential groove 61. The circumferential groove extends over a partial circumference, has a closed bottom and is concentric to the pivoting axis 11.

Figure 18:
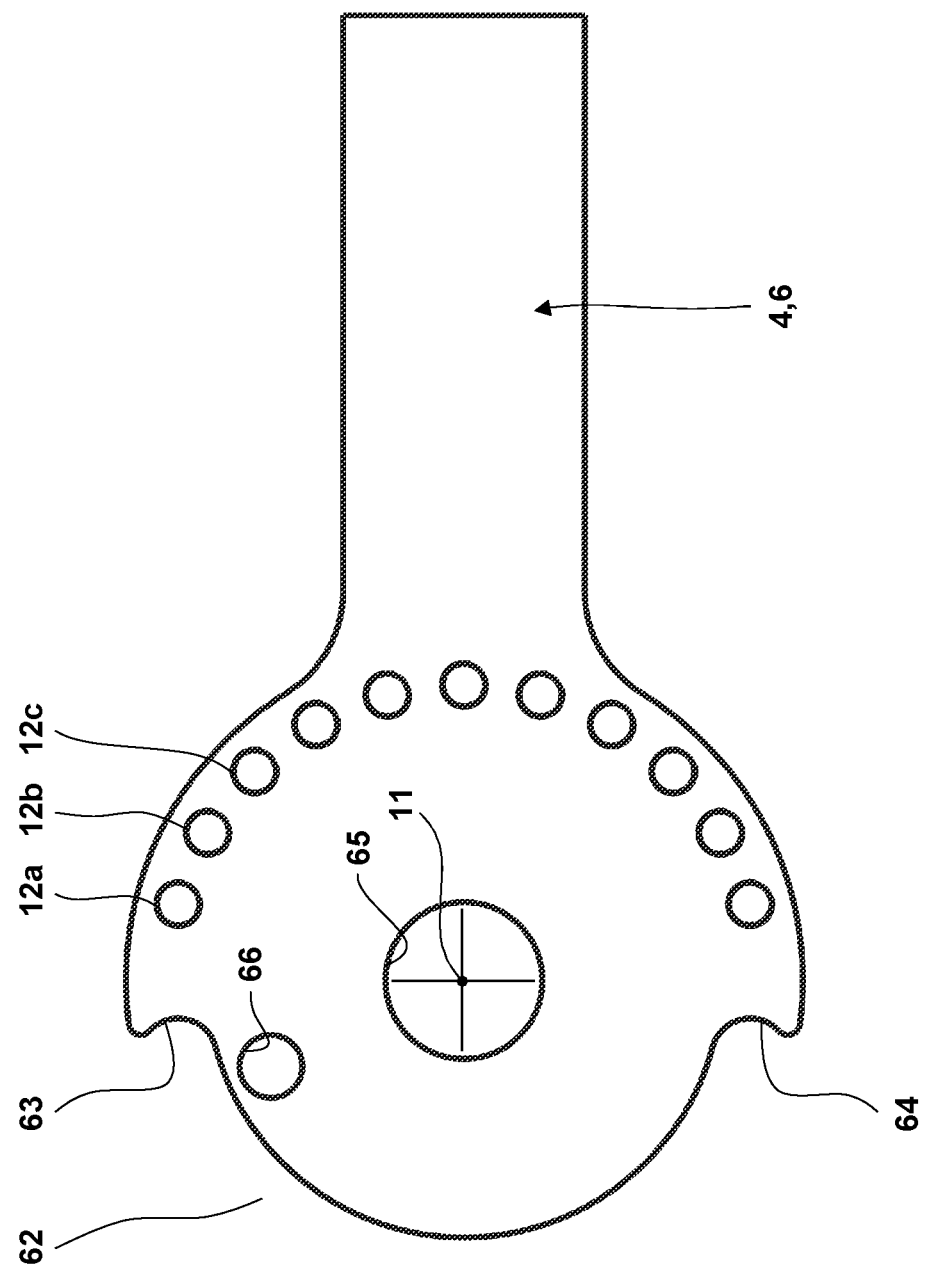

From the single-part drawing according to FIG. 18 of the splint part 6 is can be seen that the splint part 6, too, in the region of the joint 2 is generally realized in the shape of circular disc. The splint part 6, too, has a circumferential recess 62 with a reduced radius which is in both circumferential directions limited by counter-stops 63, 64. Through the bores 65 the plate screw 9 can extend, so that the bore 65 also defines the pivoting axis 11. On the side of the circular-disc shaped end region of the splint part 6 turned towards the base body 4, the splint part 6 has several bores 12a, 12b, . . . distributed over the circumference. Furthermore, the splint part 6 has a through bore 66 which is arranged radially on the inner side from the circumferential recess 62 neighboring the counter-stop 63. The cross section of the through bore 66 is coordinated with the largest diameter of the recess 54 or corresponds to it. With respect to the position, the distance from the pivoting axis 11, a possible circumferential extension of the circumferential recess 50, the counter-stops 51, 52, the recess 54, the threaded bore 53, the circumferential recess 58, the counter-stops 59, 60, the circumferential groove 61, the circumferential recess 62, the counter-stops 63, 64 and the through bore 66 reference is made to the figures. However, also deviations with regard to the shown angles and dimensions of e.g. ±5% or ±10% are possible.

Figure 14:
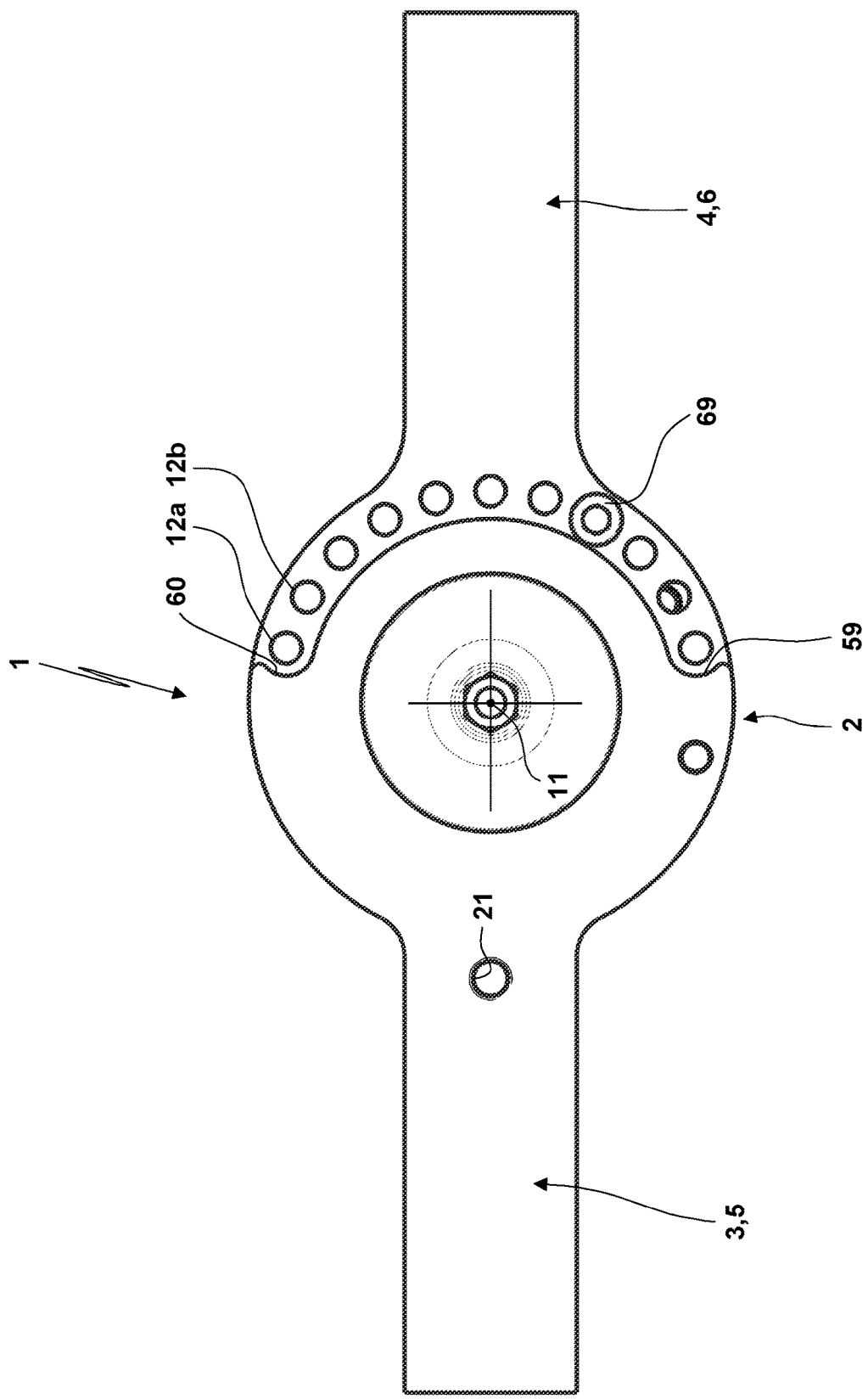
FIG. 14 shows a rear view of another embodiment of a dynamic correction splint in a straightened position.
Figure 15:
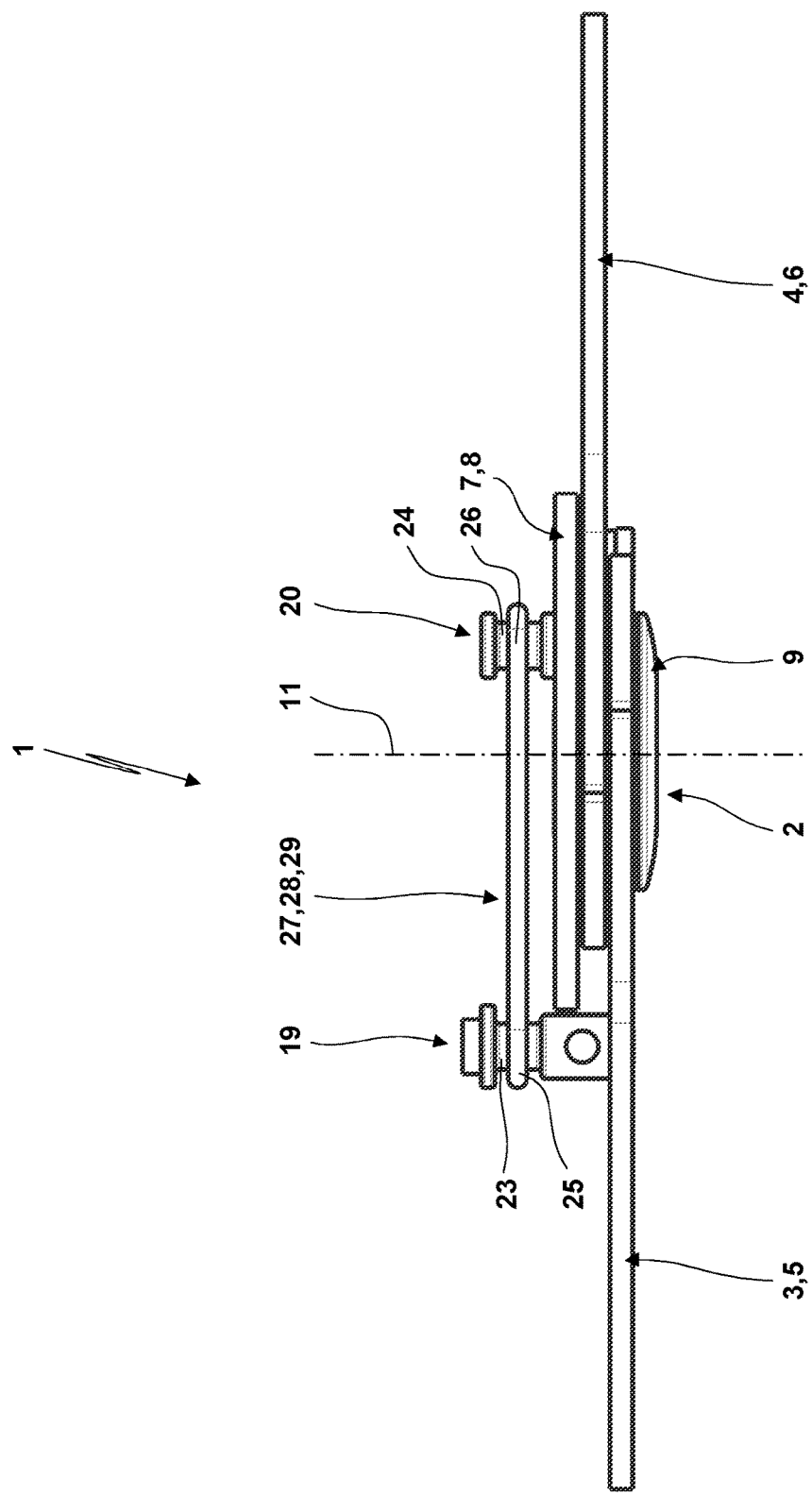
FIG. 15 shows the dynamic correction splint according to FIG. 14 in a side view.
Figure 19:
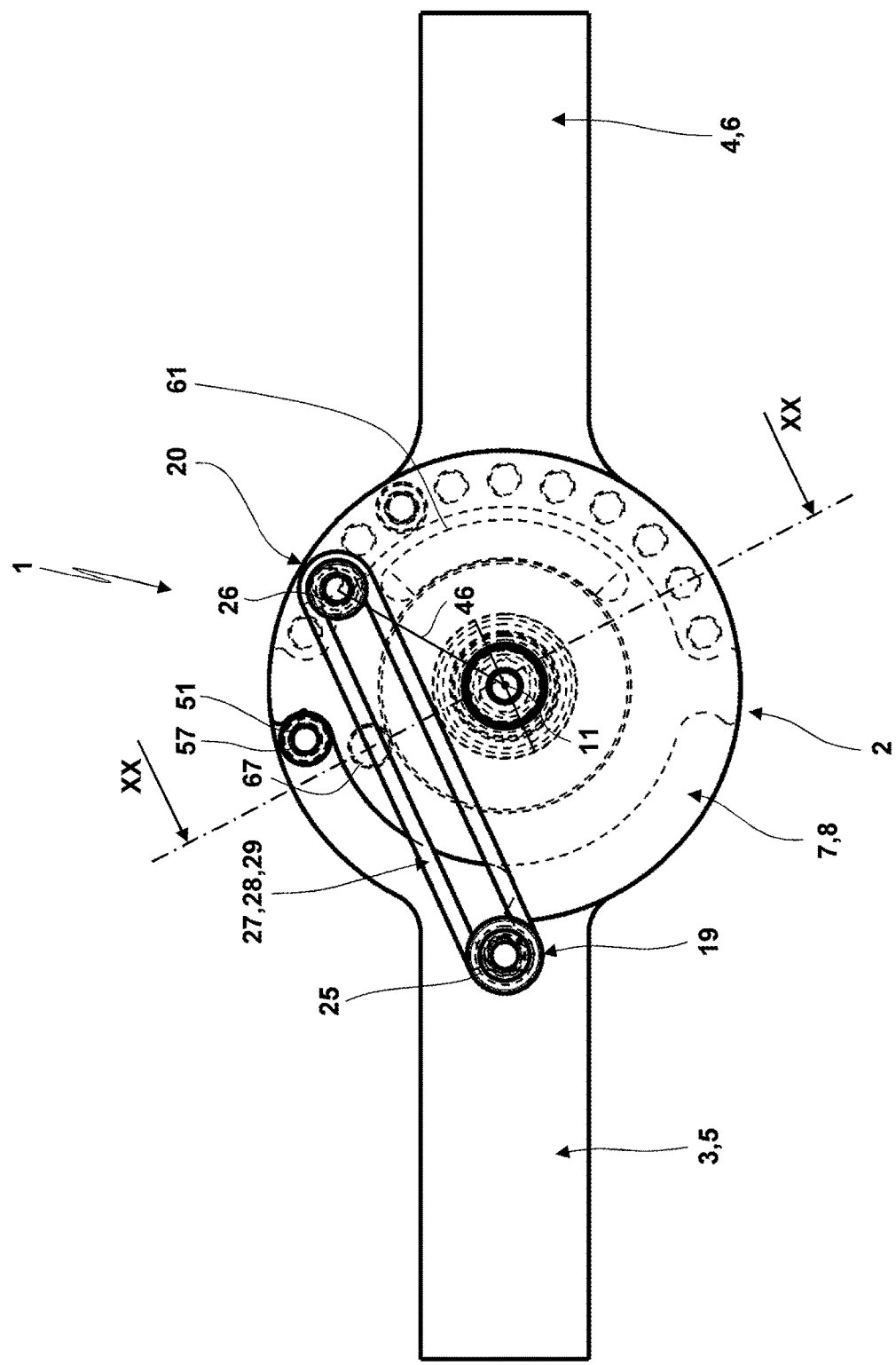
FIG. 19 shows a front view of a dynamic correction splint according to FIGS. 14 and 15.

FIGS. 14, 15 and 19 show the dynamic correction splint 1 in a mounted state in the straightened position, which is the correction position here. The plate screw 9 rotatably connects the splint parts 5, 6. The supporting bolt 19 has been screwed into the threaded bore 21, The other supporting bolt 20 has been screwed into the threaded bore 53 of the supporting disc 8. The spring device 27 has been hooked into the grooves 23, 24 of the supporting bolts 19, 20 in a pre-tensioned way. The stop 57 screwed into the threaded bore 56 via the spring device 27 is being pulled against the counter-stop 51 of the supporting disc 8. Since for this switching state of the switching device 40 (which will be explained further in the following) the supporting disc 8 is fixedly connected to the splint part 6, in this way the straightened position or correction position of the dynamic correction splint 1 is defined. From this correction position, in FIG. 19 the splint part 6 can be pivoted relatively to the splint part 5 in a clockwise direction, which goes along with an increase of the spring force in the spring device 27 but a simultaneous decrease of the lever arm and the motion of the stop 57 away from the counter-stop 51.

Figure 20:
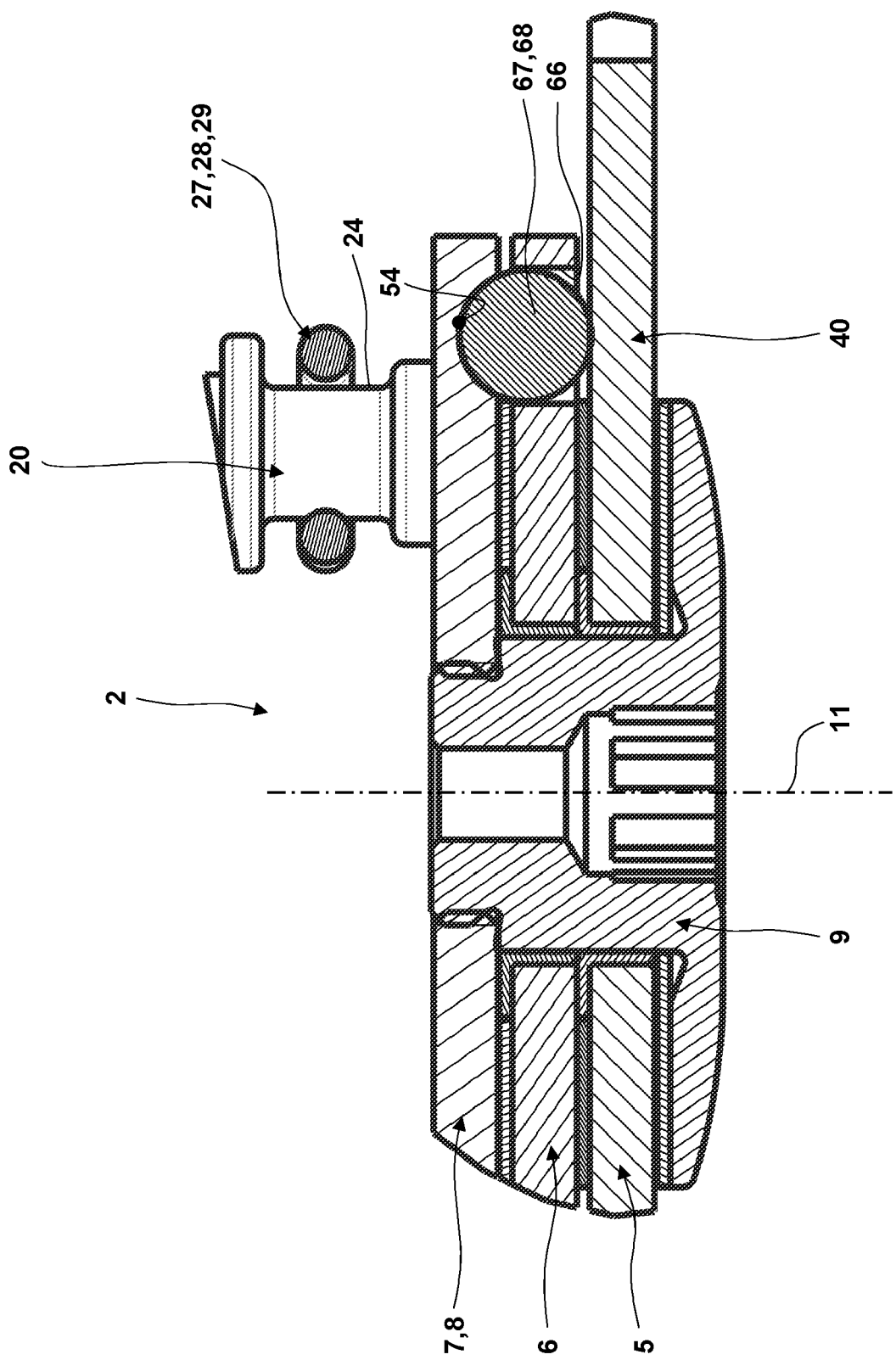
FIG. 20 shows a section XX-XX (cp.

For this embodiment the switching device 40 comprises a coupling body 67 actuated in a motion-controlled way (here, a locking ball 68). In the first pivoting range, in which a correction moment is created, the coupling body 67 fixedly couples the supporting disc 8 to the spring part 6. In the second pivoting range after the switching of the switching device 40 the coupling body 67 is disengaged between the supporting disc 8 and the splint part 6. As can be seen in FIG. 20, in order to achieve this, the locking ball 68 is accommodated form-fittingly in the recess 54 and extends from the recess 54 into the through bore 66. In this way a form-locking between the supporting disc 8 and the splint part 6 has been achieved. The locking ball 68 is caught in the recess 54 and the through bore 66, since it rests against the splint part 5 on the side turned away from the supporting disc 8. Accordingly, the locking ball 68 is not able to leave the recess 54.

Figure 21:
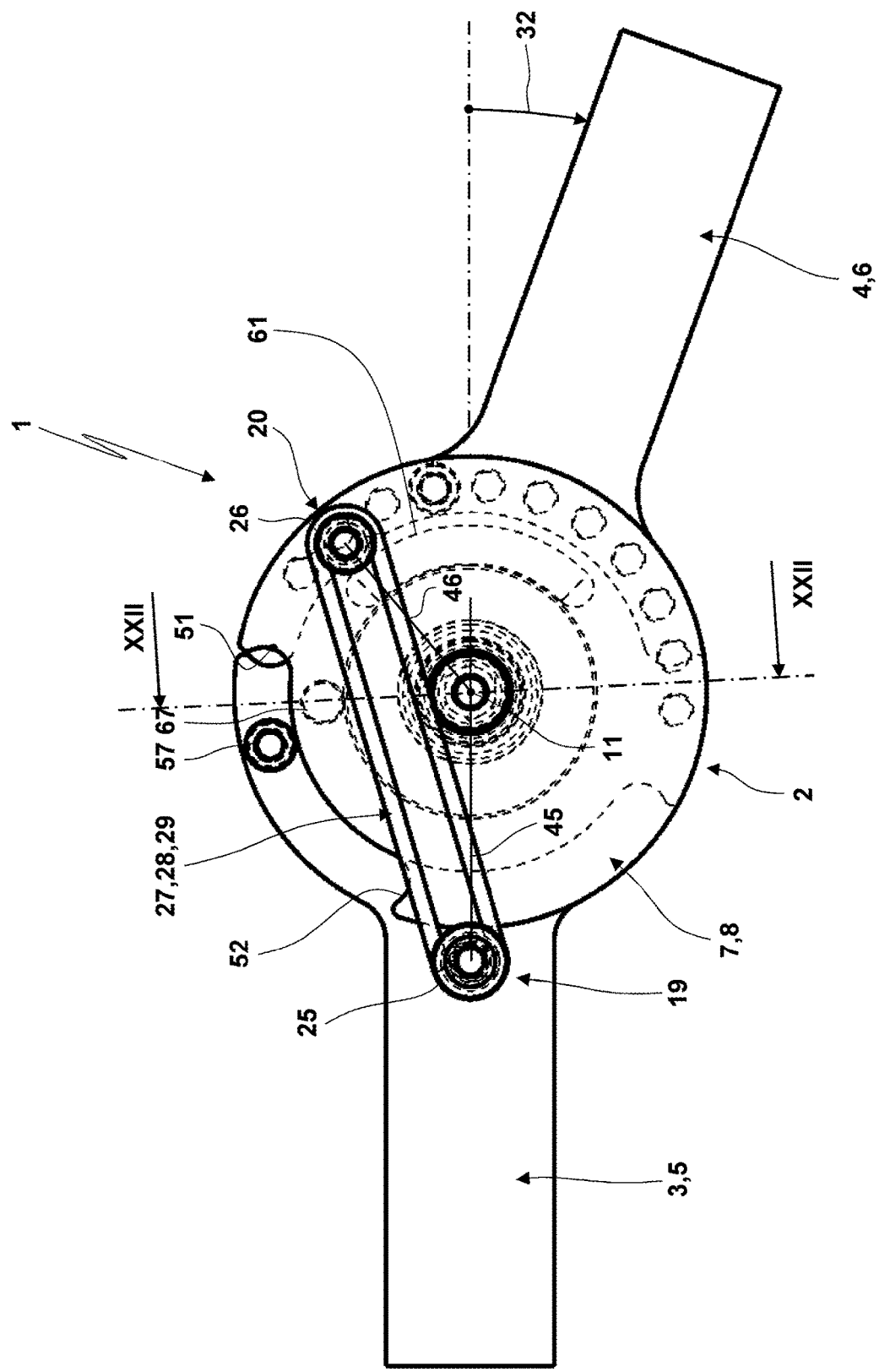
FIGS. 21 to 28 show the dynamic correction splint according to FIGS. 14, 15, 19, 20 in different bending positions, where FIGS. 21, 23, 25 and 27 each show a front view, while FIGS. 22, 24, 26 and 28 each show a corresponding section through the dynamic correction splint in the corresponding bending position.
Figure 22:
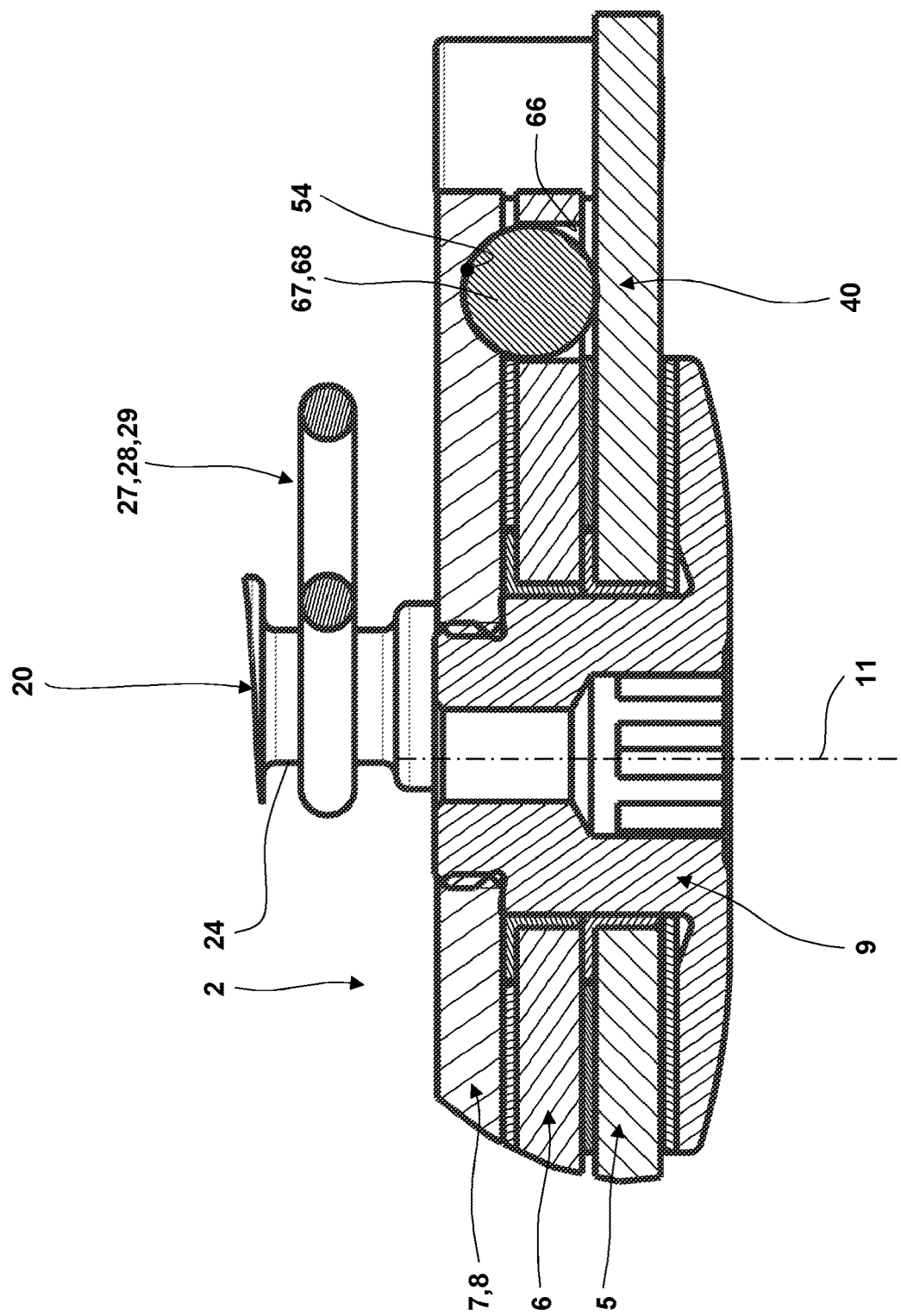
Figure 23:
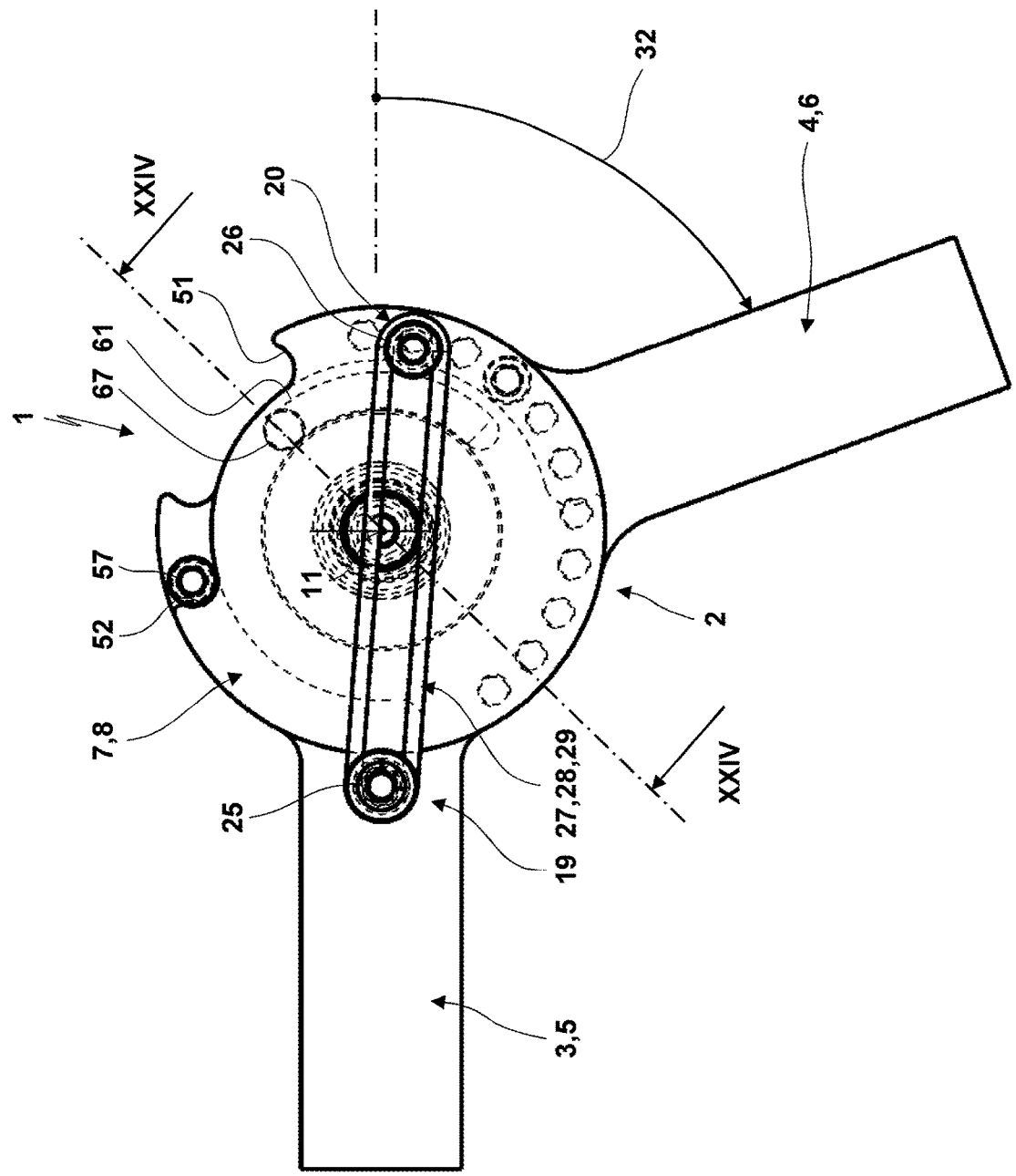
Figure 24:
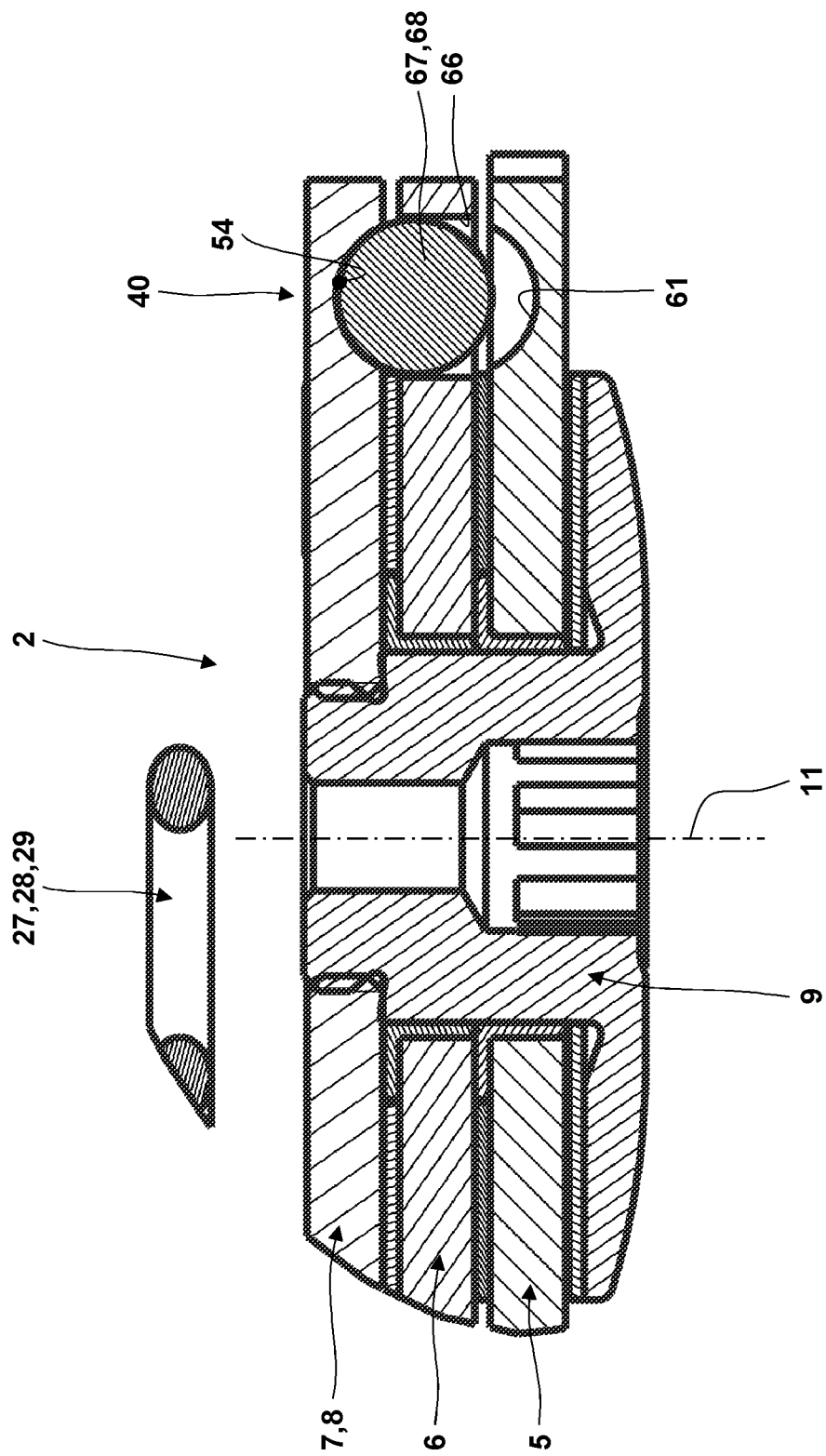
Figure 25:
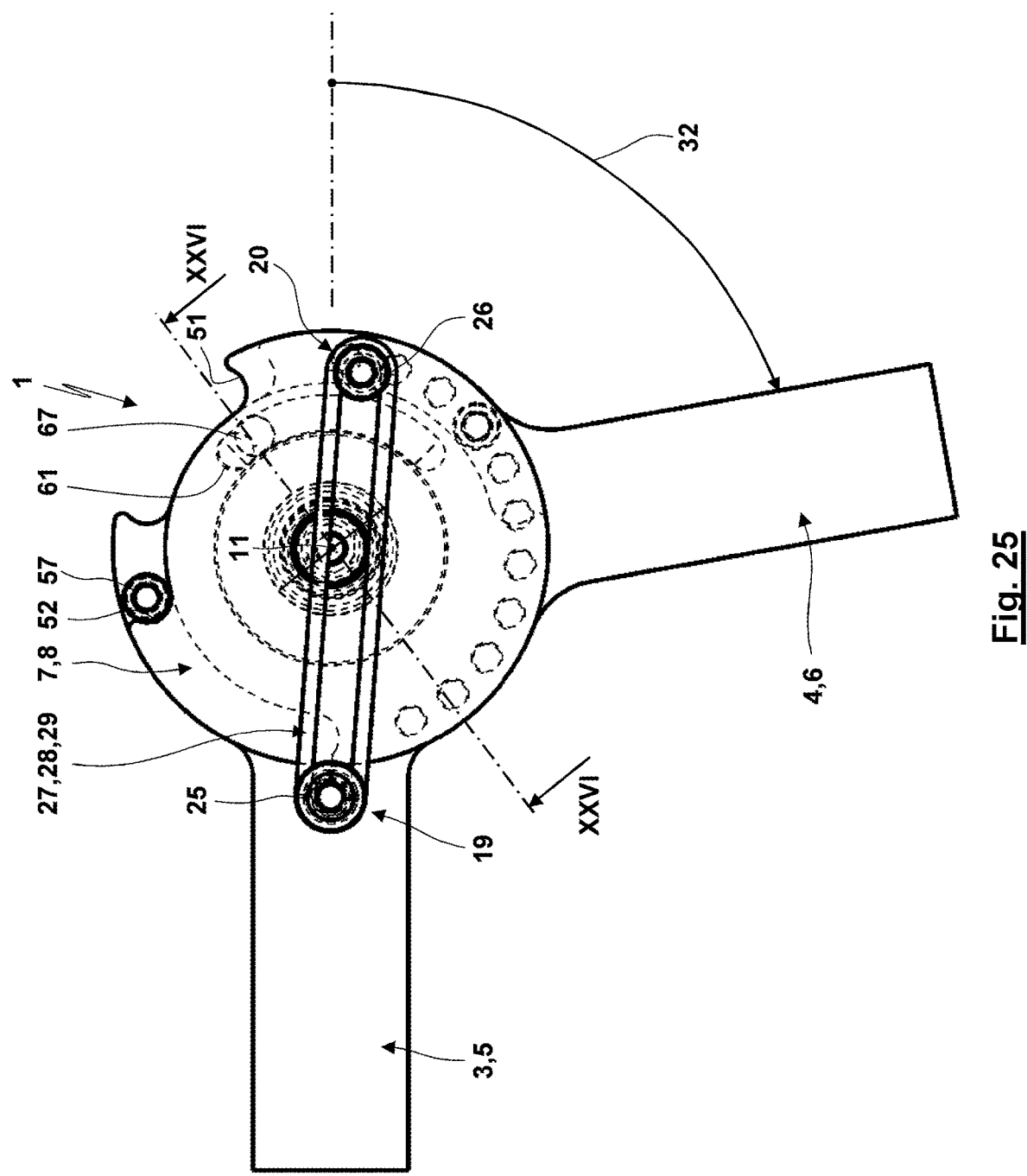
Figure 26:
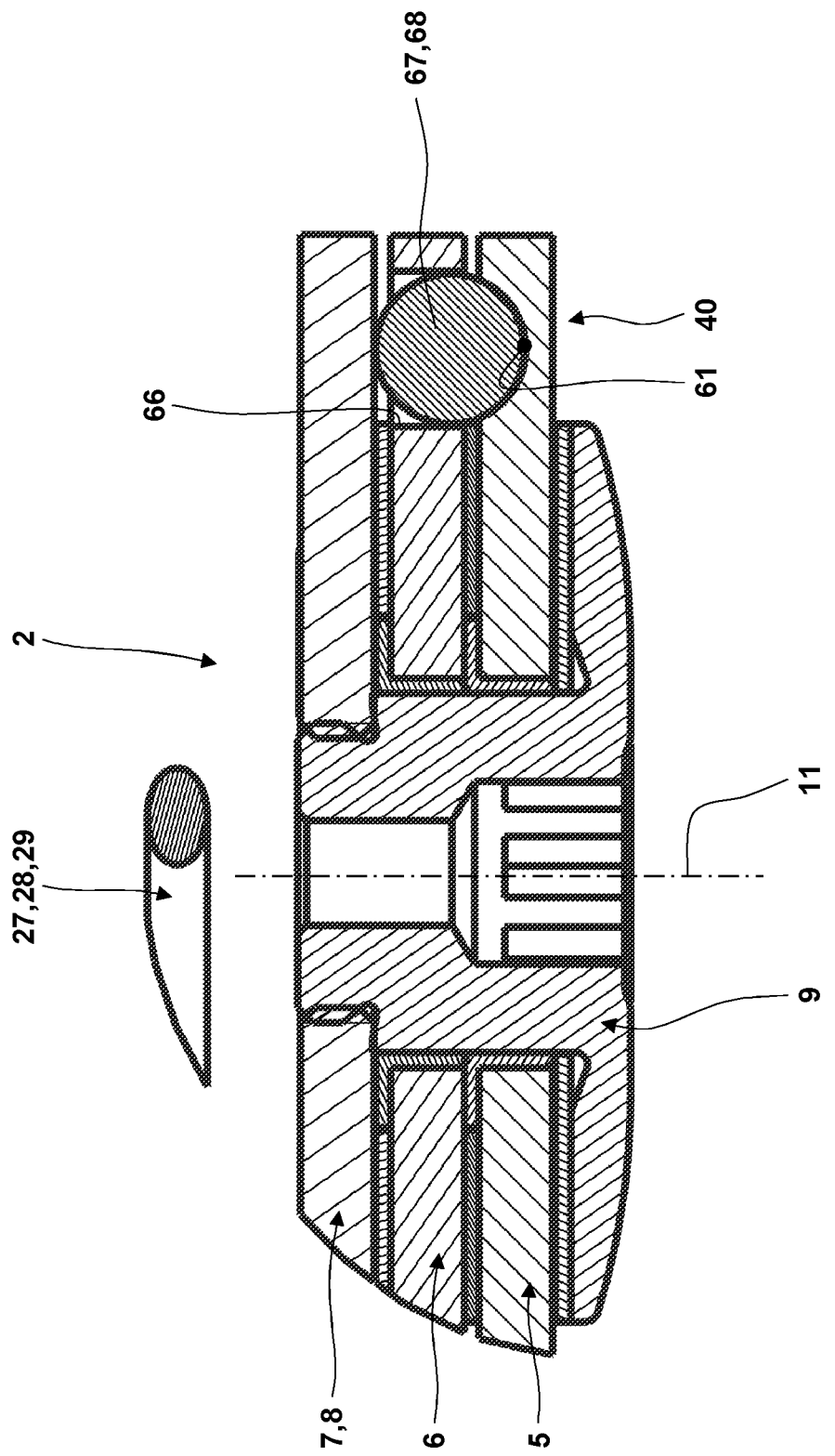
Figure 27:
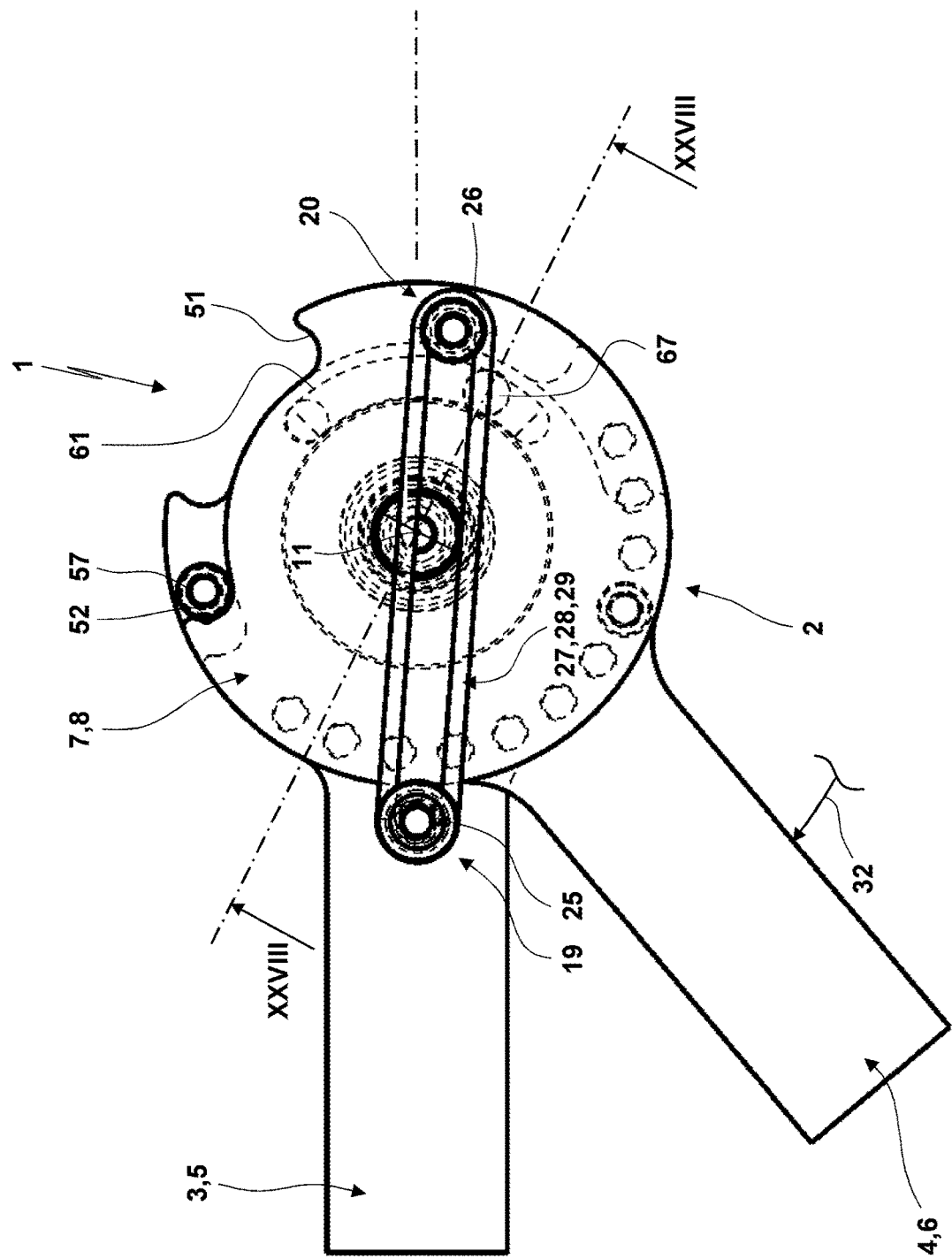
Figure 28:
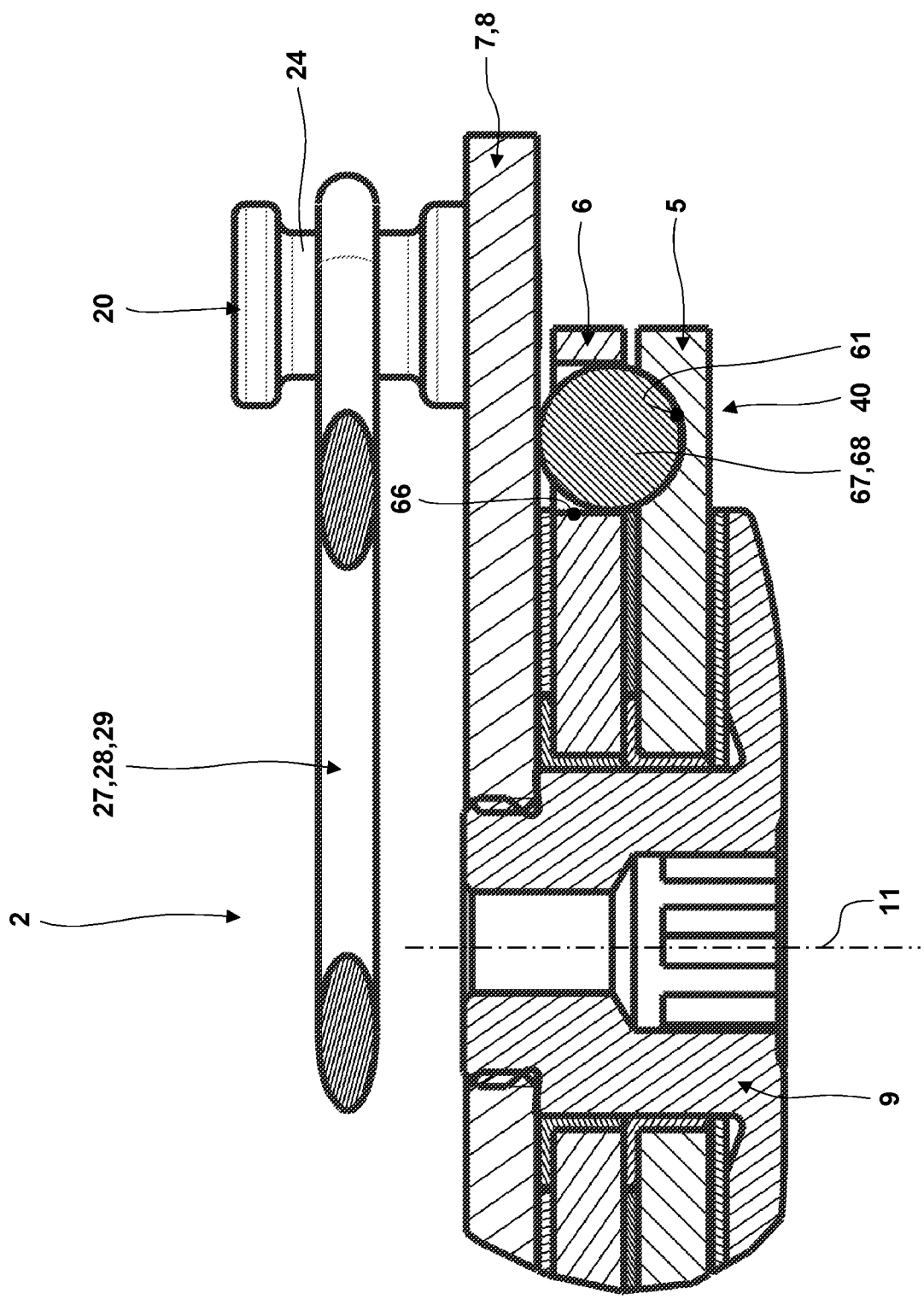

For an increase of the bending angle 32 to a pivoting position of the dynamic correction splint 1 according to FIG. 21, the locking ball 68 of the switching mechanism 40 is still caught in the recess 54 and the through bore 66. Therefore, the spring force of the spring device 27 (possibly an increased spring force) acts onto the supporting disc 8 with a decreased lever arm and via the switching mechanism 40 with the locking ball 68 onto the splint part 6 with an effective direction for reducing the bending angle 32. A transition 39 with an actuation of the switching mechanism 40 has been reached when by further increase of the bending angle 32 with the pivoting of the splint part 6 the locking ball 68 comes into the region of the circumferential groove 61 of the splint part 5 (cp. FIGS. 23 and 24). The moment exerted onto the supporting disc 8 by the spring device 27 is active onto the inclined surfaces of the recess 54, in which way the locking ball 68 is pressed into the through bore 66 and moves through the through bore 66 into the circumferential groove 61. In this way the locking of the supporting disc 8 with respect to the splint part 6 is released (cp. FIGS. 25 and 26).

When by means of an actuation of the switching mechanism 40 the locking between the supporting disc 8 and the splint part 6 has been released, generally the spring device 27 could freely rotate the supporting disc 8. Such a rotation with a pressure relief of the spring device 27, however, is impeded by the stop 57 coming to rest against the counter-stop 52. In order to achieve this, it is necessary that the unlocking of the switching mechanism 40 is done at a point in time at which the rotation of the supporting disc 8 due to the increase of the bending angle 32 has advanced to an extend such that the supporting bolts 19, 20 have already passed the position in which their connecting axis ran through the pivoting axis 11 (cp. FIG. 23).

When the switching mechanism 40 has been actuated, that is, when the locking ball 68 has been released from the supporting disc 8, there can be a further increase of the bending angle 32 with the pivoting of the splint parts 5, 6 without there being a pivoting of the supporting disc 8 connected with it, so that the position and extension of the spring device 27 does not change. An increase of the bending angle 32 in this second pivoting range is therefore achieved without there being a necessity for the user to apply a special moment or even an increasing moment. It can be seen from the direction of effect of the spring device 27 for the increase of the bending angle 32 in the first pivoting range before the actuation of the switching mechanism 40 that due to the decrease of the lever arm the correction moment becomes successively smaller at least when getting closer to the transition 39 with the actuation of the switching mechanism 40.

In the first pivoting range, in which the correction moment is created, the coupling 43 of the splint parts 5, 6 to the spring device is formed by the coupling of the splint part 5 to the spring base 25 via the supporting bolt 19, while the coupling of the splint part 6 is achieved via the locked switching mechanism 40, the supporting disc 8 and the supporting bolt 20 fixed to it with the spring base 26 of the spring device 27. At the actuation of the switching mechanism 40, an alteration into a coupling 44 occurs in that the locking of the supporting disc 8 with the splint part 6 is released, in which way a coupling of the pivoting motion of the splint part 6 with the spring device 27 is no longer present.

For the description of the embodiment according to FIGS. 14 to 28, for construction elements with the same technical realization and/or corresponding technical function to some extent the same reference signs have been used as for the embodiment of the dynamic correction splint 1 according to FIGS. 1 to 10.

For the embodiment according to FIGS. 14 to 28, an adaption of the dynamic correction splint 1 to different uses on the one hand can be done by a choice of the circumferential angle at which the supporting bolt 20 is fixed to the supporting disc 8. On the other hand, by choice of the bore 12, onto which a stop 69 is mounted which comes to rest against the counter-stop 60 to set the maximum bending angle 32, the maximum bending angle 32 can be set.

Preferably, the maximum correction moment and/or the correction moment in the correction position is in the range of 2 Nm to 8 Nm, especially in the range of 3 Nm to 6 Nm.

In the case that the dynamic correction splint is a Quengel splint, the correction position is the Quengel position, the correction force is the Quengel force, the correction moment is the Quengel moment and the correction effect is the Quengel effect.

Many variations and modifications may be made to the preferred embodiments of the invention without departing substantially from the spirit and principles of the invention. All such modifications and variations are intended to be included herein within the scope of the present invention, as defined by the following claims.

I claim:

1. Dynamic correction splint comprising:
    first and second splint parts connected via a joint for being pivoted about a pivoting axis, the joint being configured to be set to a correction position in which the first and second splint parts are at a maximum straightened angle relative to one another and to allow the first and second splint parts to pivot relative to one another over a pivoting range of bending angles from the maximum straightened angle to a maximum bending angle, the pivoting range of bending angles comprising first and second pivoting ranges of bending angles, the maximum straightened angle being at an end of the first pivoting range, the maximum bending angle being at an end of the second pivoting range;
    a spring device comprising first and second spring bases and a longitudinal spring, the longitudinal spring extending in between the first and second spring bases, the spring device being coupled to the first and second splint parts by the first and second spring bases, respectively, the spring device applying a correction moment to at least one of the first and second splint parts that depends on the bending angle during pivoting of the first and second splint parts relative to one another; and
    wherein
    the dynamic correction splint switches from a first switching state to a second switching state when the first and second splint parts are pivoted relative to one another resulting in the longitudinal spring coming to rest against a support surface of the joint, wherein the dynamic correction splint is in the first switching state during pivoting of the first and second splint parts over the first pivoting range and is in the second switching state during pivoting of the first and second splint parts over the second pivoting range, and wherein a maximum of the correction moment occurs when the dynamic correction splint is in the first switching state and a minimum of the correction moment occurs when the dynamic correction splint is in the second switching state.

2. Dynamic correction splint according to claim 1, wherein
    a) by the switching mechanism
        aa) in the first switching state the longitudinal spring is coupled to the first and second splint parts only via the first and second spring bases, respectively, of the longitudinal spring and
        ab) in the second switching state the longitudinal spring is additionally supported on a support at a location of the longitudinal spring between the first and second spring bases and the longitudinal spring is deflected by the support.

3. Dynamic correction splint according to claim 2, wherein the additional support of the longitudinal spring is arranged in the region of the pivoting axis of the first and second splint parts.

4. Dynamic correction splint according to claim 1, wherein the spring device is configured and coupled to the first and second splint parts in such a way that a characteristic of the correction moment in dependence on a bending angle of the first and second splint parts comprises a kink or a step.

5. Dynamic correction splint according to claim 1, wherein at least one of the correction position and a starting position of the dynamic correction splint is defined by a stop.

6. Dynamic correction splint according to claim 1, wherein at least one of the first and second splint parts and a supporting body of the dynamic correction splint is realized by a panel construction.

7. Dynamic correction splint according to claim 1, wherein in the second pivoting range the absolute value of the correction moment is
    a) constant,
    b) zero or
    c) at maximum is 30% of the mean of the absolute value of the correction moment in the first pivoting range.

8. Dynamic correction splint according to claim 7, wherein in the first pivoting range the correction moment
    a) has an absolute value which increases for a pivoting towards the correction position and
    b) comprises an effective direction biasing the first and second splint parts to be pivoted towards the correction position.

9. Dynamic correction splint according to claim 1, wherein in the first pivoting range the correction moment
    a) has an absolute value which increases for a pivoting towards the correction position and
    b) comprises an effective direction biasing the first and second splint parts to be pivoted towards the correction position.

10. Dynamic correction splint according to claim 1, wherein at least one of
    a) a characteristic of the correction moment,
    b) the spring device and
    c) the coupling of the spring device to the first and second splint parts is adjustable.

11. Dynamic correction splint according to claim 1, wherein
    a) the first and second spring bases of the spring device are coupled to the first and second splint parts, respectively, with an eccentricity with respect to the pivoting axis, b) the first and second splint parts form an angle larger than 180° while an angle of connecting axes of the first and second spring bases to the pivoting axis is smaller than 180°.

\* \* \* \* \*